(12) United States Patent
Jachmann et al.

(10) Patent No.: US 8,003,650 B2
(45) Date of Patent: Aug. 23, 2011

(54) HYDRAZIDE COMPOUND AND HARMFUL ARTHROPOD-CONTROLLING AGENT CONTAINING THE SAME

(75) Inventors: Markus Jachmann, Kobe (JP); Hiroshi Ikegami, Ikeda (JP); Yoshihiko Nokura, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 125 days.

(21) Appl. No.: 12/594,499

(22) PCT Filed: Apr. 10, 2008

(86) PCT No.: PCT/JP2008/057065
§ 371 (c)(1),
(2), (4) Date: Oct. 2, 2009

(87) PCT Pub. No.: WO2008/126890
PCT Pub. Date: Oct. 23, 2008

(65) Prior Publication Data
US 2010/0048578 A1 Feb. 25, 2010

(30) Foreign Application Priority Data
Apr. 12, 2007 (JP) .................. 2007-104647

(51) Int. Cl.
| | | |
|---|---|---|
| A61K 31/501 | (2006.01) | |
| A61K 31/4439 | (2006.01) | |
| A61K 31/415 | (2006.01) | |
| C07D 401/02 | (2006.01) | |
| C07D 403/02 | (2006.01) | |
| C07D 231/10 | (2006.01) | |

(52) U.S. Cl. ................ 514/252.05; 514/341; 514/406; 544/238; 548/365.1; 548/373.1

(58) Field of Classification Search .......... 514/252.05, 514/341, 406; 544/238; 546/275.4, 276.4; 548/365.1, 373.1
See application file for complete search history.

(56) References Cited

U.S. PATENT DOCUMENTS

| | | | |
|---|---|---|---|
| 4,985,461 | A | 1/1991 | Hsu et al. |
| 5,756,524 | A | 5/1998 | Riordan et al. |
| 6,747,047 | B2 | 6/2004 | Lahm et al. |
| 6,995,178 | B2 | 2/2006 | Lahm et al. |
| 7,199,138 | B2 | 4/2007 | Finkelstein et al. |
| 2003/0229050 | A1 | 12/2003 | Lahm et al. |
| 2004/0142984 | A1 | 7/2004 | Lahm et al. |
| 2004/0209923 | A1 | 10/2004 | Berger et al. |
| 2005/0075372 | A1 | 4/2005 | Lahm et al. |
| 2005/0282868 | A1 | 12/2005 | Finkelstein et al. |
| 2006/0079561 | A1 | 4/2006 | Lahm et al. |
| 2007/0203201 | A1 | 8/2007 | Finkelstein et al. |

FOREIGN PATENT DOCUMENTS

| | | |
|---|---|---|
| JP | 62-167747 A | 7/1987 |
| JP | 9-510471 A | 10/1997 |
| JP | 2003-528070 A | 9/2003 |
| JP | 2004-538327 A | 12/2004 |
| JP | 2005-502716 A | 1/2005 |
| JP | 2005-503384 A | 2/2005 |
| WO | WO 03/016284 A1 | 2/2003 |
| WO | WO-2007/043677 A1 | 4/2007 |

OTHER PUBLICATIONS

Japanese International Search Report issued in PCT/JP2008/057065 mailed May 20, 2008.
Tetsuya Toya et al., "Cyclic Dibenzoylhydrazines Reproducing the Conformation of Ecdysone Agonists, RH-5849", Bioorganic & Medicinal Chemistry 10, 2002, pp. 953-961..
English translation of International Preliminary Report on Patentability and Written Opinion of the International Search Authority (Forms PCT/IB/338, PCT/IB/373 andPCT/ISA/237) issued on Oct. 22, 2009 in PCT/JP2008/057065.
Extended European Search Report issued on Feb. 17, 2011 in corresponding European Patent Application No. 08 74 0166.

*Primary Examiner* — Rebecca Anderson
*Assistant Examiner* — Samantha Shterengarts
(74) *Attorney, Agent, or Firm* — Birch, Stewart, Kolasch & Birch, LLP

(57) ABSTRACT

Disclosed is a hydrazine compound represented by the formula (1) below, which has an excellent control activity against a harmful arthropod. (1) (In the formula, $R^1$, $R^5$, $R^6$ and $R^7$ represent a hydrogen atom or the like; $R^2$ and $R^3$ are bonded together at their ends to form a 5- to 8-membered ring together with two nitrogen atoms; $R^4$ represents a halogen atom or the like; J represents 1-(3-chloro-2-pyridyl)-3-bromo-1H-pyrazol-5-yl group or the like; and M represents a hydrogen atom, an optionally halogenated $C_1$-$C_6$ alkyl group, or the like.)

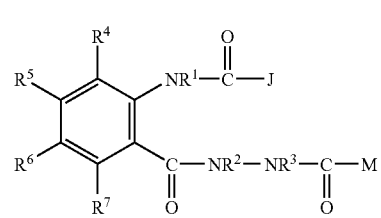

(1)

10 Claims, No Drawings

HYDRAZIDE COMPOUND AND HARMFUL ARTHROPOD-CONTROLLING AGENT CONTAINING THE SAME

TECHNICAL FIELD

The present invention relates to a hydrazide compound and a harmful arthropod controlling agent containing the same.

BACKGROUND ART

WO 01/70671, WO 03/015518, WO 03/016284, WO 03/016300 and WO 03/024222 disclose certain amide compounds for controlling harmful arthropods.

DISCLOSURE OF THE INVENTION

Problems to be Solved by the Invention

An object of the present invention is to provide a hydrazide compound represented by the following formula (1) which has an excellent controlling activity on harmful arthropods.

Means for Solving the Problem

As a result of the present inventors' intensively study, they have found a hydrazide compound represented by the following formula (1) (hereinafter, sometimes, referred to as the present compound) which has an excellent controlling activity on harmful arthropods, and thus the present invention has been completed.

That is, the present invention provides:
<1> A hydrazide compound represented by the formula (1):

[Chemical Formula 1]

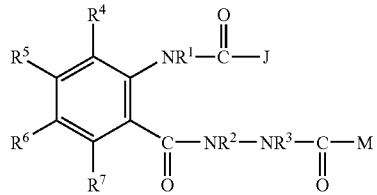

(1)

wherein
R$^1$ represents a hydrogen atom, an optionally halogenated C1-C6 alkyl group, a C2-C6 cyanoalkyl group, a C2-C6 alkoxyalkyl group, an optionally halogenated C3-C6 alkenyl group, an optionally halogenated C3-C6 alkynyl group, or a C7-C9 phenylalkyl group whose benzene ring moiety may be substituted with a substituent A shown below;

R$^2$ and R$^3$ are bound at their terminal ends to represent —Z—, and two nitrogen atoms to which R$^2$ and R$^3$ are attached together with Z form a 5- to 8-membered ring, p0 {in which Z is formed by binding a plurality of groups selected from the group consisting of (a) —CH$_2$—, (b) —CH=CH—, (c) —CO—, (d) an oxygen atom, (e) —S(C)$_n$— and (f) —NR$^a$—;

Z may be substituted on its carbon atom(s) with a substituent selected from the group consisting of a halogen atom, an optionally halogenated C1-C6 alkyl group, and an optionally halogenated C2-C6 alkoxycarbonyl group;

n represents an integer of 0 to 2;

R$^a$ represents a hydrogen atom, an optionally halogenated C1-C6 alkyl group, an optionally halogenated C2-C6 alkoxycarbonyl group, or a phenyl group optionally substituted with a substituent A shown below};

R$^4$ represents a halogen atom, or an optionally halogenated C1-C6 alkyl group;

each of R$^5$, R$^6$ and R$^7$ independently represents a hydrogen atom, a halogen atom, a cyano group, or an optionally halogenated C1-C6 alkyl group, or R$^5$ and R$^6$ may be combined to form a 1,3-butadiene-1,4-diyl group optionally substituted with a substituent C shown below;

M represents —R$^8$, —OR$^9$, —SR$^{10}$ or —NR$^{11}$R$^{12}$,
{in which R$^8$ represents a hydrogen atom, an optionally halogenated C1-C6 alkyl group, a C2-C6 alkoxyalkyl group, an optionally halogenated C2-C6 alkenyl group, or an optionally halogenated C2-C6 alkynyl group;

each of R$^9$, R$^{10}$, R$^{11}$ and R$^{12}$ independently represents an optionally halogenated C1-C6 alkyl group, a C3-C6 alkoxyalkyl group, an optionally halogenated C3-C6 alkenyl group, or an optionally halogenated C3-C6 alkynyl group};

J represents any one of J1 to J3 shown below,

[Chemical Formula 2]

J1:

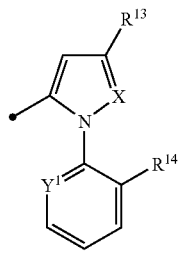

J2:

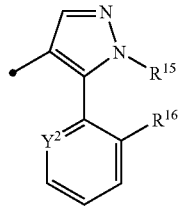

J3:

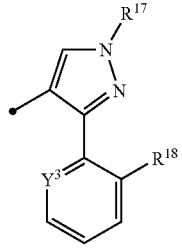

wherein X represents a nitrogen atom or CR$^{19}$;
Y$^1$ represents a nitrogen atom or CR$^{20}$;
Y$^2$ represents a nitrogen atom or CR$^{21}$;
Y$^3$ represents a nitrogen atom or CR$^{21}$;
Y$^3$ represents a nitrogen atom or CR$^{22}$;
R$^{13}$ and R$^{19}$ each independently represents a hydrogen atom, a halogen atom, a cyano group, an optionally halogenated C1-C6 alkyl group, an optionally halogenated C1-C6 alkoxy group, an optionally halogenated C1-C6 alkylthio group, an optionally halogenated C1-C6 alkylsulfinyl group, or an optionally halogenated C1-C6 alkylsulfonyl group;

$R^{15}$ and $R^{17}$ each independently represents an optionally halogenated C1-C6 alkyl group;

$R^{14}, R^{16}, R^{18}, R^{20}, R^{21}$ and $R^{22}$ each independently represents a hydrogen atom, a halogen atom, or an optionally halogenated C1-C6 alkyl group};

substituent A: a substituent selected from the group consisting of a halogen atom, a cyano group, a nitro group, an optionally halogenated C1-C6 alkyl group, and an optionally halogenated C1-C6 alkoxy group; and substituent C: a substituent selected from the group consisting of a halogen atom, a cyano group, and an optionally halogenated C1-C6 alkyl group;

<2> The hydrazide compound according to <1>, wherein, in the formula (1), Z is any one of Z1 to Z4 shown below:

Z1: —$(CR^{31}R^{32})_m$—
Z2: —$CR^{33}R^{34}$—$CR^{35}$=$CR^{36}$—$CR^{37}R^{38}$—
Z3: —$(CR^{39}R^{40})_2$-Q-$(CR^{41}R^{42})_2$—
Z4: —$(CR^{44}R^{45})_p$—C(=O)—$(CR^{46}R^{47})_q$— in which each of $R^{31}, R^{32}, R^{33}, R^{34}, R^{35}, R^{36}, R^{37}, R^{38}, R^{39}, R^{40}, R^{41}, R^{42}, R^{44}, R^{45}, R^{46}$ and $R^{47}$ independently represents a hydrogen atom or a C1-C4 alkyl group, m represents an integer of 3 to 5, Q represents an oxygen atom, —S(O)$_n$— or —$NR^{43}$— {n represents an integer of 0 to 2, and $R^{43}$ represents a C1-C4 alkyl group}, and p and q each independently represents an integer of 0 to 4, provided that the sum of p and q is 2 to 4;

<3> The hydrazide compound according to <2>, wherein, in the formula (1), Z is any one of Z1 to Z3;

<4> The hydrazide compound according to <2>, wherein, in the formula (1), Z is Z1 or Z4;

<5> The hydrazide compound according to <2>, wherein, in the formula (1), Z is Z1;

<6> The hydrazide compound according to <1>, wherein, in the formula (1), the ring formed by two nitrogen atoms to which $R^2$ and $R^3$ are attached, together with Z is a 5- or 6-membered ring;

<7> The hydrazide compound according to <1>, wherein, in the formula (1), Z is a group formed by binding a plurality of groups selected from the group consisting of (a) —CH$_2$— and (c) —CO— (in which Z may be substituted on its carbon atom(s) with a substituent selected from the group consisting of a halogen atom, an optionally halogenated C1-C6 alkyl group, and an optionally halogenated C2-C6 alkoxycarbonyl group;

<8> The hydrazide compound according to <1>, wherein, in the formula (1), Z is a C3-C6 polymethylene group;

<9> A harmful arthropod controlling agent comprising the hydrazide compound according to any one of <1> to <8> as an active ingredient;

<10> Use of the hydrazide compound according to any one of <1> to <8> as an active ingredient of a harmful arthropod controlling agent;

<11> A method for controlling harmful arthropods, which comprises applying the hydrazide compound according to any one of <1> to <8> directly to harmful arthropods, or applying to habitats of harmful arthropods; and <12> Use of the hydrazide compound according to any one of <1> to <8> for the production of a harmful arthropod controlling agent.

EFFECT OF THE INVENTION

The present compound has an excellent controlling activity on harmful arthropods and is therefore useful as an active ingredient of a harmful arthropod controlling agent.

BEST MODE FOR CARRYING OUT THE INVENTION

In the present invention, examples of the "halogen atom" include a fluorine atom, a chlorine atom, a bromine atom and an iodine atom.

Examples of the "C3-C6 polymethylene group" include a trimethylene group, a tetramethylene group, a pentamethylene group and a hexamethylene group.

Examples of the "C1-C4 alkyl group" include a methyl group, an ethyl group, a propyl group, a butyl group, an isopropyl group, an isobutyl group, a sec-butyl group and a tert-butyl group.

Examples of the "optionally halogenated C1-C6 alkyl group" include a methyl group, a trifluoromethyl group, a trichloromethyl group, a chloromethyl group, a dichloromethyl group, a fluoromethyl group, a difluoromethyl group, an ethyl group, a pentafluoroethyl group, a 2,2,2-trifluoroethyl group, a 2,2,2-trichloroethyl group, a propyl group, an isopropyl group, a heptafluoroisopropyl group, a butyl group, an isobutyl group, a sec-butyl group, a tert-butyl group, a pentyl group and a hexyl group.

Examples of the "optionally halogenated C2-C6 alkenyl group" include a vinyl group, a 1-propenyl group, a 2-propenyl group, a 1-methylvinyl group, a 2-chlorovinyl group and a 2-methyl-1-propenyl group.

Examples of the "optionally halogenated C3-C6 alkenyl group" include a 2-propenyl group, a 3-chloro-2-propenyl group, a 2-chloro-2-propenyl group, a 3,3-dichloro-2-propenyl group, a 3-bromo-2-propenyl group, a 2-bromo-2-propenyl group, a 3,3-dibromo-2-propenyl group, a 2-butenyl group, a 3-butenyl group, a 1-methyl-2-propenyl group, a 2-methyl-2-propenyl group, a 3-methyl-2-butenyl group, a 2-pentenyl group and a 2-hexenyl group.

Examples of the "optionally halogenated C2-C6 alkynyl group" include an ethynyl group, a 2-propynyl group, a 3-chloro-2-propynyl group, a 3-bromo-2-propynyl group, a 1-methyl-2-propynyl group, a 2-butynyl group and a 3-butynyl group.

Examples of the "optionally halogenated C3-C6 alkynyl group" include a 2-propynyl group, a 3-chloro-2-propynyl group, a 3-bromo-2-propynyl group, a 1-methyl-2-propynyl group, a 2-butynyl group and a 3-butynyl group.

Examples of the "C2-C6 cyanoalkyl group" include a cyanomethyl group, a 1-cyanoethyl group, a 2-cyanoethyl group, a 2-cyanopropyl group, a 1-cyano-2-propyl group, a 1-cyano-2-methyl-2-propyl group, a 3-cyano-2-butyl group, a 3-cyanopropyl group and a 4-cyanobutyl group.

Examples of the "C2-C6 alkoxyalkyl group" include a methoxymethyl group, a 1-methoxyethyl group, a 2-methoxyethyl group, a 2-ethoxyethyl group and a 2-isopropyloxyethyl group.

Examples of the "C3-C6 alkoxyalkyl group" include a 2-methoxyethyl group, a 2-ethoxyethyl group and a 2-isopropyloxyethyl group.

Examples of the "C2-C6 alkoxycarbonyl group" include a methoxycarbonyl group, an ethoxycarbonyl group, an isopropoxycarbonyl group and a tert-butoxycarbonyl group.

Examples of the "1,3-butadiene-1,4-diyl group optionally substituted with a substituent C" include a 1,3-butadiene-1,4-diyl group, a 2-bromo-1,3-butadiene-1,4-diyl group, a 2-chloro-1,3-butadiene-1,4-diyl group, a 2-cyano-1,3-butadiene-1,4-diyl group and a 1-methyl-1,3-butadiene-1,4-diyl group.

Examples of the "optionally halogenated C1-C6 alkoxy group" include a methoxy group, a trifluoromethoxy group, an ethoxy group, a 2,2,2-trifluoroethoxy group, a propyloxy group, an isopropyloxy group, a butoxy group, an isobutyloxy group, a sec-butoxy group, a tert-butoxy group, a pentyloxy group and a hexyloxy group.

Examples of the "optionally halogenated C1-C6 alkylthio group" include a methylthio group, a trifluoromethylthio group and an ethylthio group.

Examples of the "optionally halogenated C1-C6 alkylsulfinyl group" include a methylsulfinyl group, a trifluoromethylsulfinyl group and an ethylsulfinyl group.

Examples of the "optionally halogenated C1-C6 alkylsulfonyl group" include a methylsulfonyl group, a trifluoromethylsulfonyl group and an ethylsulfonyl group.

Examples of the "phenyl group optionally substituted with a substituent A" include a phenyl group, a 2-chlorophenyl group, a 3-chlorophenyl group, a 4-chlorophenyl group, a 4-fluorophenyl group, a 4-bromophenyl group, a 4-iodophenyl group, a 2-cyanophenyl group, a 3-cyanophenyl group, a 4-cyanophenyl group, a 2-nitrophenyl group, a 3-nitrophenyl group, a 4-nitrophenyl group, a 2-methylphenyl group, a 3-methylphenyl group, a 4-methylphenyl group, a 2-(trifluoromethyl)phenyl group, a 3-(trifluoromethyl)phenyl group, a 4-(trifluoromethyl)phenyl group, a 2-methoxyphenyl group, a 3-methoxyphenyl group, a 4-methoxyphenyl group, a 4-(trifluoromethoxy)phenyl group and a 4-(methylthio)phenyl group.

Examples of the "C7-C9 phenylalkyl group whose benzene ring moiety may be substituted with a substituent A" include a benzyl group, a 1-phenylethyl group, a 2-phenylethyl group, a 2-chlorobenzyl group, a 3-chlorobenzyl group, a 4-chlorobenzyl group, a 4-bromobenzyl group, a 2-cyanobenzyl group, a 3-cyanobenzyl group, a 4-cyanobenzyl group, a 2-nitrobenzyl group, a 3-nitrobenzyl group, a 4-nitrobenzyl group, a 2-methylbenzyl group, a 3-methylbenzyl group, a 4-methylbenzyl group, a 2-methoxybenzyl group, a 3-methoxybenzyl group and a 4-methoxybenzyl group.

Examples of the 5- to 8-membered ring formed by two nitrogen atoms to which $R^2$ and $R^3$ are attached together with Z include rings shown below:

[Chemical Formula 3]

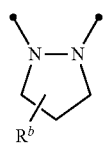
T1

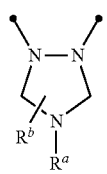
T2

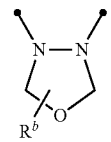
T3

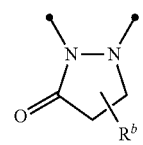
T4

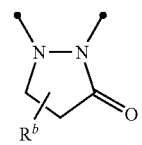
T5

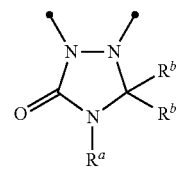
T6

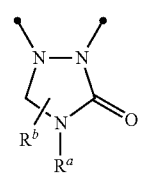
T7

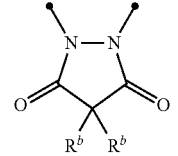
T8

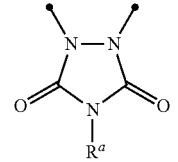
T9

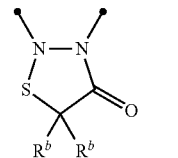
T10

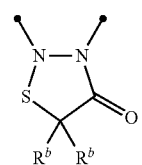
T11

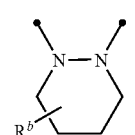
T12

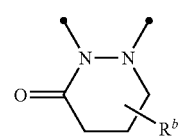

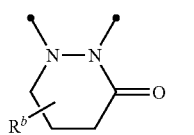 T13
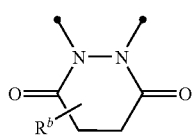 T14
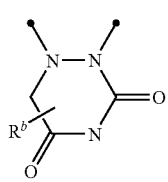 T15
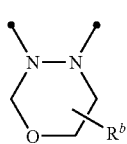 T16
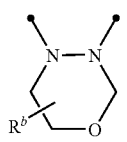 T17
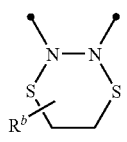 T18
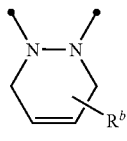 T19
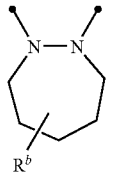 T20
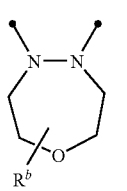 T21
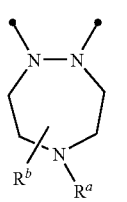 T22
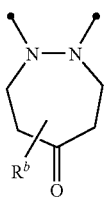 T23
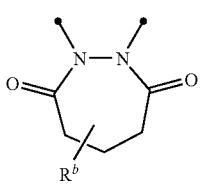 T24
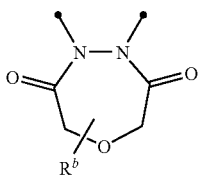 T25
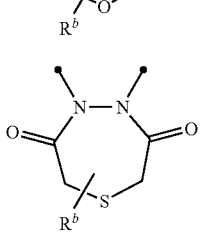 T26
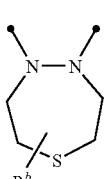 T27
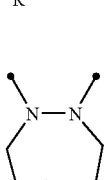 T28
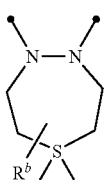 T29
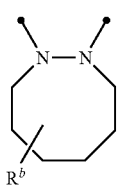 T30

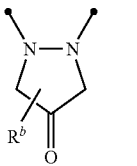
T31

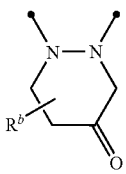
T32

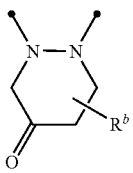
T33

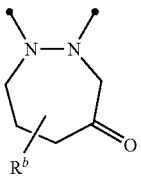
T34

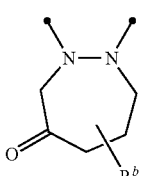
T35 wherein $R^a$ represents a hydrogen atom, an optionally halogenated C1-C6 alkyl group, an optionally halogenated alkoxycarbonyl group, or a phenyl group optionally substituted with a substituent A shown above, and $R^b$ represents a hydrogen atom, a halogen atom, an optionally halogenated C1-C6 alkyl group, or an optionally halogenated C2-C6 alkoxycarbonyl group.

Examples of the present compound include the following aspects:

"Aspect 1"

A hydrazide compound represented by the formula (1), wherein Z is any one of Z1 to Z3 shown below:

Z1: —$(CR^{31}R^{32})_m$—
Z2: —$CR^{33}R^{34}$—$CR^{35}$=$CR^{36}$—$CR^{37}R^{38}$—
Z3: —$(CR^{39}R^{40})_2$-Q-$(CR^{41}R^{42})_2$— in which $R^{31}$, $R^{32}$, $R^{33}$, $R^{34}$, $R^{35}$, $R^{36}$, $R^{37}$, $R^{38}$, $R^{39}$, $R^{40}$ each of $R^{91}$ and $R^{42}$ independently represents a hydrogen atom, or a C1-C4 alkyl group;

m represents an integer of 3 to 5; and

Q represents an oxygen atom, —S(O)$_n$—, or —$NR^{43}$.

{n represents an integer of 0 to 2, and $R^{43}$ represents a C1-C4 alkyl group}.

"Aspect 2"

A hydrazide compound represented by the formula (1), wherein $R^2$ and $R^3$ are bound at their terminal ends to form —Z—, and Z is Z1 shown below:

Z1: —$(CR^{31}R^{32})_m$— wherein each of $R^{31}$ and $R^{32}$ independently represents a hydrogen atom, or a C1-C4 alkyl group, and m represents an integer of 3 to 5.

"Aspect 3"

A hydrazide compound represented by the formula (1), wherein $R^2$ and $R^3$ are bound at their terminal ends to form —Z—, and Z is a C3-C6 polymethylene group.

"Aspect 4"

A hydrazide compound represented by the formula (1), wherein $R^1$ is a hydrogen atom.

"Aspect 5"

A hydrazide compound represented by the formula (1), wherein $R^1$ is a hydrogen atom, $R^2$ and $R^3$ are bound at their terminal ends to form —Z—, and Z is a C3-C6 polymethylene group optionally substituted with a C1-C4 alkyl group.

"Aspect 6"

A hydrazide compound represented by the formula (1), wherein J is J1.

"Aspect 7"

A hydrazide compound represented by the formula (1), wherein M is —$R^8$ or —$OR^9$.

"Aspect 8"

A hydrazide compound represented by the formula (1), wherein $R^1$ is a hydrogen atom or an optionally halogenated C1-C6 alkyl group; $R^2$ and $R^3$ are bound at their terminal ends to form —Z—, and Z is a C3-C6 polymethylene group; $R^4$ is a halogen atom or an optionally halogenated C1-C6 alkyl group; $R^5$, $R^6$ and $R^7$ each independently represents a hydrogen atom, a halogen atom, cyano group or an optionally halogenated C1-C6 alkyl group; M is —$R^8$, —$OR^9$ or —$NR^{11}R^{12}$; $R^8$ is a hydrogen atom or an optionally halogenated C1-C6 alkyl group; $R^9$ is an optionally halogenated C1-C6 alkyl group; each of $R^{11}$ and $R^{12}$ independently represents an optionally halogenated C1-C6 alkyl group; J is J1; X is a nitrogen atom or CH; $Y^1$ is a nitrogen atom or CH; $R^{13}$ is a hydrogen atom, a halogen atom, a cyano group, an optionally halogenated C1-C6 alkyl group, an optionally halogenated C1-C6 alkoxy group or an optionally halogenated C1-C6 alkylthio group; and $R^{14}$ is a hydrogen atom, a halogen atom or an optionally halogenated C1-C6 alkyl group.

"Aspect 9"

A hydrazide compound represented by the formula (1), wherein $R^1$ is a hydrogen atom or a methyl group; $R^2$ and $R^3$ are bound at their terminal ends to form —Z—, and Z is a C3-C6 polymethylene group; $R^4$ is a halogen atom or a methyl group; $R^5$ and $R^7$ are hydrogen atoms; $R^6$ is a hydrogen atom, a halogen atom, a cyano group or a methyl group; M is a hydrogen atom, a methyl group, a methoxy group or a dimethylamino group; J is J1; X is a nitrogen atom or CH; $Y^1$ is a nitrogen atom; $R^{13}$ is a halogen atom, a cyano group or a trifluoromethyl group; and $R^{14}$ is a halogen atom.

"Aspect 10"

A hydrazide compound represented by the formula (1), wherein the ring formed by two nitrogen atoms to which $R^2$ and $R^3$ are attached together with Z is a 5- or 6-membered ring.

"Aspect 11"

A hydrazide compound represented by the formula (1), wherein the ring formed by two nitrogen atoms to which $R^2$ and $R^3$ are attached together with Z is a 5-membered ring.

"Aspect 12"

A hydrazide compound represented by the formula (1), wherein Z is a group formed by binding a plurality of groups selected from the group consisting of (a) —$CH_2$— and (c) —CO— (in which Z may be substituted on its carbon atom(s) with a substituent selected from the group consisting of a halogen atom, an optionally halogenated C1-C6 alkyl group and an optionally halogenated C2-C6 alkoxycarbonyl group).

"Aspect 13"

A hydrazide compound represented by the formula (1), wherein the ring formed by combining two nitrogen atoms to which $R^2$ and $R^3$ are attached, and Z is a 5- or 6-membered ring, and Z is a group formed by binding a plurality of groups selected from the group consisting of (a) —$CH_2$— and (c) —CO— (in which Z may be substituted with a substituent selected from the group consisting of a halogen atom, an optionally halogenated C1-C6 alkyl group, and an optionally halogeanted C2-C6 alkoxycarbonyl group on the carbon atom).

"Aspect 14"

A hydrazide compound represented by the formula (1), wherein the ring formed by two nitrogen atoms to which $R^2$ and $R^3$ are attached together with Z is a 5-membered ring, and Z is a group formed by binding a plurality of groups selected from the group consisting of (a) —$CH_2$— and (c) —CO— (in which Z may be substituted on its carbon atom(s) with a substituent selected from the group consisting of a halogen atom, an optionally halogenated C1-C6 alkyl group, and an optionally halogenated C2-C6 alkoxycarbonyl group).

"Aspect 15"

A hydrazide compound represented by the formula (1), wherein Z is any one of Z1 to Z4 shown below:
Z1: —$(CR^{31}R^{32})_m$—
Z2: —$CR^{33}R^{34}$—$CR^{35}$=$CR^{36}$—$CR^{37}R^{38}$—
Z3: —$(CR^{39}R^{40})_2$-Q-$(CR^{41}R^{42})_2$—
Z4: —$(CR^{44}R^{45})_p$—$C(=O)$—$(CR^{46}R^{47})_q$—
in which each of $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{44}$, $R^{45}$, $R^{46}$ and $R^{47}$ independently represents a hydrogen atom or a C1-C4 alkyl group, m represents an integer of 3 to 5, Q represents an oxygen atom, —$S(O)_n$— or —$NR^{43}$— {in which n represents an integer of 0 to 2 and $R^{43}$ represents a C1-C4 alkyl group}, and each of p and q independently represents an integer of 0 to 4, provided that the sum of p and q is 2 to 4.

"Aspect 16"

A hydrazide compound represented by the formula (1), wherein Z(s) are Z1 or Z4 shown below:
Z1: —$(CR^{31}R^{32})_m$—
Z4: —$(CR^{44}R^{45})_p$—$C(=O)$—$(CR^{46}R^{47})_q$—
in which each of $R^3$, $R^1$, $R^3R^2$, $R^{44}$ and $R^{45}$ independently represents a hydrogen atom or a C1-C4 alkyl group, m represents an integer of 3 to 5, and each of p and q independently represents an integer of 0 to 4, provided that the sum of p and q is 2 to 4.

"Aspect 17"

A hydrazide compound represented by the formula (1), wherein Z is Z4 shown below:
Z4:—$(CR^{44}R^{45})_p$—$C(=O)$—$(CR^{46}R^{47})_q$—
in which each of $R^{44}$, $R^{45}$, $R^{46}$ and $R^{47}$ independently represents a hydrogen atom or a C1-C4 alkyl group, and p and q each independently represents an integer of 0 to 4, provided that the sum of p and q is 2 to 4.

"Aspect 18"

A hydrazide compound represented by the formula (1), wherein $R^1$ is a hydrogen atom, M is —$OR^9$ and J is J1.

"Aspect 19"

A hydrazide compound represented by the formula (1), wherein $R^1$ is a hydrogen atom, Z is any one of Z1 to Z4 shown above, M is —$OR^9$ and J is J1.

"Aspect 20"

A hydrazide compound represented by the formula (1), wherein $R^1$ is a hydrogen atom, Z is any one of Z1 to Z4 shown above, M is —$OR^9$ and J is J1.

"Aspect 21"

A hydrazide compound represented by the formula (1), wherein $R^1$ is a hydrogen atom, Z is Z1 or Z4 shown above, M is —$OR^9$ and J is J1.

"Aspect 22"

A hydrazide compound represented by the formula (1), wherein $R^1$ is a hydrogen atom, the ring formed by two nitrogen atoms to which $R^2$ and $R^3$ are attached together with Z is a 5- or 6-membered ring, M is —$OR^9$ and J is J1.

"Aspect 23"

A hydrazide compound represented by the formula (1), wherein $R^1$ is a hydrogen atom, the ring formed by two nitrogen atoms to which $R^2$ and $R^3$ are attached together with Z is a 5-membered ring, M is —$OR^9$ and J is J1.

Hereinafter, a process for producing the present compound will be explained.

The present compound can be produced, for example, by the following Process A-1 to Process C-3.

(Process A-1)

The present compound can be produced by reacting a compound represented by the formula (2):

[Chemical Formula 4]

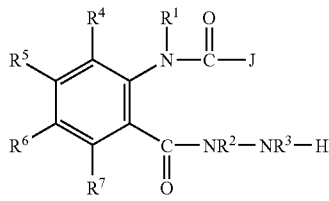

(2)

wherein $R^1$, $R^2$, $R^3$, $R^4$, $R^5$, $R^6$, $R^7$ and J are as defined above (hereinafter referred to as the compound (2)) with a compound represented by the formula (3):

[Chemical Formula 5]

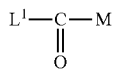

(3)

wherein M is as defined above and $L^1$ represents a halogen atom or an M-C(=O)O— group (hereinafter referred to as the compound (3)).

The reaction is carried out in the presence or the absence of a solvent. Examples of the solvent used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methylpyrrolidone, 1,3-dimethyl-2-imidadzolidinone, and dimethyl sulfoxide; and a mixture thereof.

The amount of the compound (3) used in the reaction is usually from 1 to 2 mol per mol of the compound (2). The reaction is carried out in the presence of a base, if necessary. Examples of the base when the reaction is carried out in the presence of the base include nitrogen-containing heterocyclic compounds such as pyridine, picoline, 2,6-lutidine, 1,8-diazabicyclo[5,4,0]7-undecene (DBU), and 1,5-diazabicyclo[4,3,0]5-nonene (DBN); tertiary amines such as triethylamine, and N,N-diisopropylethylamine; and inorganic bases such as potassium carbonate, and sodium hydride. The amount of the base when the reaction is carried out in the presence of the base is usually from 1 mol or more per mol of the compound (2).

The reaction temperature is usually from 0 to 100° C. and the reaction time is usually from 0.1 to 24 hours.

After completion of the reaction, the present compound can be isolated by pouring the reaction mixture into water and extracting the mixture with an organic solvent, or collecting a deposited precipitate by filtration. The isolated present compound may be further purified, for example, by recrystallization, or chromatography.

(Process B-1)

The present compound can be produced by reacting a compound represented by the formula (6):

[Chemical Formula 6]

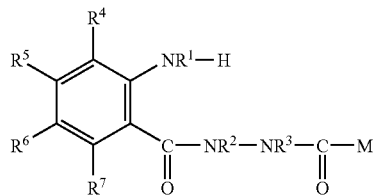
(6)

wherein $R^1$, $R^2$, $R^3$, $R^4$, $R^5$, $R^6$, $R^7$ and M are as defined above (hereinafter referred to as the compound (6)) with a compound represented by the formula (7):

[Chemical Formula 7]

(7)

wherein $L^2$ represents a halogen atom and J is as defined above (hereinafter referred to as the compound (7)).

The reaction is carried out in the presence or the absence of a solvent. Examples of the solvent used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitrites such as acetonitrile; aprotic polar solvents such as N,N-dimethylformamide, N-methylpyrrolidone, 1,3-dimethyl-2-imidadzolidinone, and dimethyl sulfoxide; and a mixture thereof.

The amount of the compound (7) used in the reaction is usually 1 mol or more per mol of the compound (6).

The reaction is carried out in the presence of a base, if necessary. Examples of the base when the reaction is carried out in the presence of the base include nitrogen-containing heterocyclic compounds such as pyridine, picoline, 2,6-lutidine, 1,8-diazabicyclo[5,4,0]7-undecene (DBU), and 1,5-diazabicyclo[4,3,0]5-nonene (DBN); tertiary amines such as triethylamine, and N,N-diisopropylethylamine; and inorganic bases such as potassium carbonate, and sodium hydride. The amount of the base when the reaction is carried out in the presence of the base is usually from 1 mol or more per mol of the compound (6).

The reaction temperature is usually from 0 to 100° C. and the reaction time is usually from 0.1 to 24 hours.

After completion of the reaction, the present compound can be isolated by pouring the reaction mixture into water and extracting the mixture with an organic solvent, or collecting a deposited precipitate by filtration. The isolated present compound may be further purified, for example, by recrystallization, or chromatography.

(Process B-2)

The present compound can be produced by reacting the compound (6) with a compound represented by the formula (8):

[Chemical Formula 8]

$$HO-\underset{\underset{O}{\|}}{C}-J \qquad (8)$$

wherein J are as defined above (hereinafter referred to as the compound (8)) in the presence of a dehydrating agent.

The reaction is carried out in the presence or the absence of a solvent. Examples of the solvent used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methylpyrrolidone, 1,3-dimethyl-2-imidadzolidinone, and dimethyl sulfoxide; and a mixture thereof.

The amount of the compound (8) used in the reaction is usually 1 mol or more per mol of the compound (6). Examples of the dehydrating agent used in the reaction include carbodiimides such as dicyclohexylcarbodiimide (DCC), and 1-ethyl-3-(3-dimethylaminopropyl)carbodiimide hydrochloride (WSC). The amount of the dehydrating agent is usually from 1 mol or more per mol of the compound (6).

The reaction temperature is usually from 0 to 100° C. and the reaction time is usually from 0.1 to 24 hours.

After completion of the reaction, the present compound can be isolated by pouring the reaction mixture into water and extracting the mixture with an organic solvent, or collecting a deposited precipitate by filtration. The isolated present compound may be further purified, for example, by recrystallization, or chromatography.

(Process B-3)

The present compound can be produced by reacting the compound (6) with a compound represented by the formula (4):

[Chemical Formula 9]

(4)

wherein J is as defined above (hereinafter referred to as the compound (4)) in the presence of an oxidizing agent, for example, peracids such as methachloroperbenzoic acid; and quinone compounds such as o-chloranil, and p-chloranil.

The reaction is carried out in the presence of a solvent. Examples of the solvent used in the reaction include ether solvents such as 1,4-dioxane, diethylether, tetrahydrofuran, and methyl tert-butyl ether; halogenated hydrocarbon solvents such as dichloromethane, chloroform, carbon tetrachloride, 1,2-dichloroethane, and chlorobenzene; hydrocarbon solvents such as hexane, heptane, toluene, benzene, and xylene; nitrile solvents such as acetonitrile; amide solvents such as N,N-dimethylformamide; nitrogen-containing cyclic compound solvents such as N-methyl pyrrolidone, and 1,3-dimethyl-2-imidazolidinone; aprotic solvents, for example, sulfoxide solvents such as dimethyl sulfoxide; carboxylic acid solvents such as acetic acid; ketone solvents such as acetone, and isobutyl methyl ketone; ester solvents such as ethyl acetate; alcohol solvents such as 2-propanol, and tert-butyl alcohol; water; and a mixture thereof.

The amount of the compound (4) used in the reaction is usually 1 mol or more per mol of the compound (6).

The reaction temperature is usually from 0 to 150° C. and the reaction time is usually from instant to 72 hours.

After completion of the reaction, the compound (1) can be isolated by pouring the reaction mixture into water and extracting the mixture with an organic solvent, or collecting a deposited precipitate by filtration. The isolated compound (1) may be further purified, for example, by recrystallization, or chromatography.

(Process C-1)

Among the present compounds, a compound represented by the formula (1-ii):

[Chemical Formula 10]

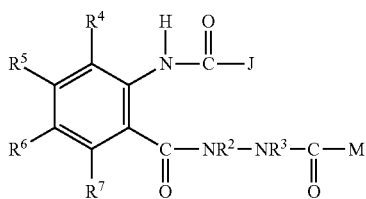

(1-ii)

wherein $R^2$, $R^3$, $R^4$, $R^5$, $R^6$, $R^7$, J and M are as defined above (hereinafter referred to as the compound (1-ii)) is produced by reacting a compound represented by the formula (9):

[Chemical Formula 11]

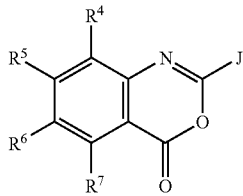

(9)

wherein $R^4$, $R^5$, $R^6$, $R^7$ and J are as defined above (hereinafter referred to as the compound (9)) with a compound represented by the formula (10):

[Chemical Formula 12]

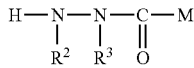

(10)

wherein $R^2$, $R^3$ and M are as defined above (hereinafter referred to as the compound (10)).

The reaction is carried out in the presence or the absence of a solvent. Examples of the solvent used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitrites such as acetonitrile; aprotic polar solvents such as N,N-dimethylformamide, N-methylpyrrolidone, 1,3-dimethyl-2-imidadzolidinone, and dimethyl sulfoxide; and a mixture thereof.

The amount of the compound (10) used in the reaction is usually 1 mol or more per mol of the compound (9).

The reaction temperature is usually from 0 to 100° C. and the reaction time is usually from 0.1 to 48 hours.

After completion of the reaction, the compound (1-ii) can be isolated by pouring the reaction mixture into water and extracting the mixture with an organic solvent, or collecting a deposited precipitate by filtration. The isolated compound (1-ii) may be further purified by, for example, recrystallization, or chromatography.

(Process C-2)

Among the present compounds, a compound represented by the formula (1-iii):

[Chemical Formula 13]

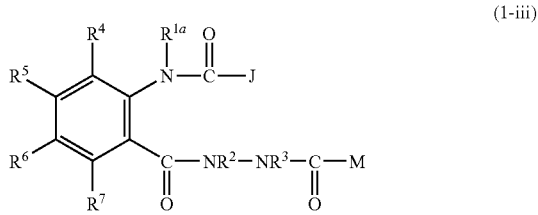

(1-iii)

wherein $R^{1a}$ represents an optionally halogenated C1-C6 alkyl group, a C2-C6 cyanoalkyl group, a C2-C6 alkoxyalkyl group, an optionally halogenated C3-C6 alkenyl group, an optionally halogenated C3-C6 alkynyl group, or a C7-C9 phenylalkyl group whose benzene ring moiety may be substituted with a substituent A, and $R^2$, $R^3$, $R^4$, $R^5$, $R^6$, $R^7$, J and M are as defined above (hereinafter referred to as the compound (1-iii)) is produced by reacting a compound represented by the formula (11):

[Chemical Formula 14]

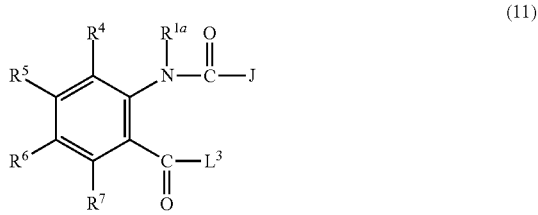

(11)

wherein $L^3$ represents a halogen atom, and $R^{1a}$, $R^4$, $R^5$, $R^6$, $R^7$ and J are as defined above (hereinafter referred to as the compound (11)) with the compound (10).

The reaction is carried out in the presence or the absence of a solvent. Examples of the solvent used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methylpyrrolidone, 1,3-dimethyl-2-imidazolidinone, and dimethyl sulfoxide; and a mixture thereof.

The amount of the compound (10) used in the reaction is usually 1 mol or more per mol of the compound (11).

The reaction is carried out in the presence of a base, if necessary. Examples of the base when the reaction is carried out in the presence of the base include nitrogen-containing heterocyclic compounds such as pyridine, picoline, 2,6-lutidine, 1,8-diazabicyclo[5,4,0]7-undecene (DBU), and 1,5-diazabicyclo[4,3,0]5-nonene (DBN); tertiary amines such as triethylamine, and N,N-diisopropylethylamine; and inorganic bases such as potassium carbonate, and sodium hydride. The amount of the base when the reaction is carried out in the presence of the base is usually from 1 mol or more per 1 mol of the compound (6).

The reaction temperature is usually from 0 to 100° C. and the reaction time is usually from 0.1 to 24 hours.

After completion of the reaction, the compound (1-iii) can be isolated by pouring the reaction mixture into water and extracting the mixture with an organic solvent, or collecting a deposited precipitate by filtration. The isolated compound (1-iii) may be further purified, for example, by recrystallization, or chromatography.

(Process C-3)

The compound (1-iii) can also be produced by reacting a compound represented by the formula (12):

[Chemical Formula 15]

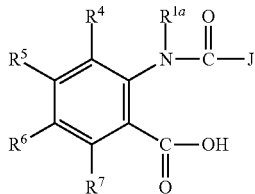

(12)

wherein $R^{1a}$, $R^4$, $R^5$, $R^6$, $R^7$ and J are as defined above (hereinafter referred to as the compound (12)) with the compound (10) in the presence of a dehydrating agent.

The reaction is carried out in the presence or the absence of a solvent. Examples of the solvent used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methylpyrrolidone, 1,3-dimethyl-2-imidazolidinone, and dimethyl sulfoxide; and a mixture thereof.

The amount of the compound (10) used in the reaction is usually 1 mol or more per mol of the compound (12).

Examples of the dehydrating agent used in the reaction include carbodiimides such as dicyclohexylcarbodiimide (DCC), and 1-ethyl-3-(3-dimethylaminopropyl)carbodiimide hydrochloride (WSC). The amount of the dehydrating agent is usually 1 mol or more per mol of the compound (12).

The reaction temperature is usually from 0 to 100° C. and the reaction time is usually from 0.1 to 24 hours.

After completion of the reaction, the compound (1-iii) can be isolated by pouring the reaction mixture into water and extracting the mixture with an organic solvent, or collecting a deposited precipitate by filtration. The isolated compound (1-iii) may be further purified, for example, by recrystallization, or chromatography.

Hereinafter, a process for producing intermediates for producing the present compound will be explained.

Among the compound (2), a compound represented by the formula (2-i):

[Chemical Formula 16]

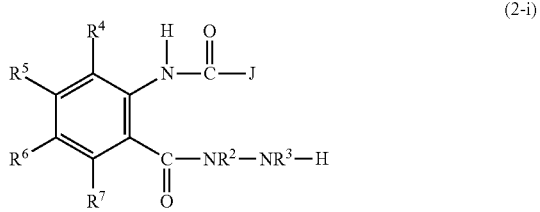

(2-i)

wherein $R^2$, $R^3$, $R^4$, $R^5$, $R^6$, $R^7$ and J are as defined above (hereinafter referred to as the compound (2-i)) can be produced by reacting the compound (9) with a compound represented by the formula (13):

[Chemical Formula 17]

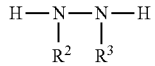

(13)

wherein $R^2$ and $R^3$ are as defined above (hereinafter referred to as the compound (13)).

The reaction is carried out in the presence or the absence of a solvent. Examples of the solvent used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitrites such as acetonitrile; aprotic polar solvents such as N,N-dimethylformamide, N-methylpyrrolidone, 1,3-dimethyl-2-imidadzolidinone, and dimethyl sulfoxide; and a mixture thereof.

The amount of the compound (13) used in the reaction is usually 1 mol or more per mol of the compound (9).

The reaction temperature is usually from −50 to 100° C. and the reaction time is usually from 0.1 to 24 hours.

After completion of the reaction, the compound (2-i) can be isolated by pouring the reaction mixture into water and extracting the mixture with an organic solvent, or collecting a deposited precipitate by filtration. The isolated compound (2-i) may be further purified, for example, by recrystallization, or chromatography.

Among the compound (2), a compound represented by the formula (2-ii):

[Chemical Formula 18]

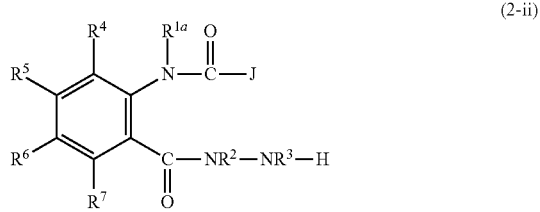

(2-ii)

wherein $R^{1a}$, $R^2$, $R^3$, $R^4$, $R^5$, $R^6$, $R^7$ and J are as defined (hereinafter referred to as the compound (2-ii)) can be produced by reacting the compound (11) with the compound (13).

The reaction is carried out in the presence or the absence of a solvent. Examples of the solvent used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitrites such as acetonitrile; aprotic polar solvents such as N,N-dimethylformamide, N-methylpyrrolidone, 1,3-dimethyl-2-imidadzolidinone, and dimethyl sulfoxide; and a mixture thereof.

The amount of the compound (13) used in the reaction is usually 1 mol or more per mol of the compound (11).

The reaction temperature is usually from −50 to 100° C. and the reaction time is usually from 0.1 to 24 hours.

After completion of the reaction, the compound (2-ii) can be isolated by pouring the reaction mixture into water and extracting the mixture with an organic solvent, or collecting a deposited precipitate by filtration. The isolated compound (2-ii) may be further purified, for example, by recrystallization, or chromatography.

The compound (9) can be produced by reacting a compound represented by the formula (14):

[Chemical Formula 19]

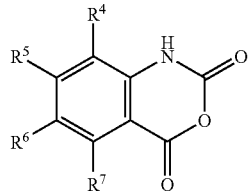

(14)

wherein $R^4$, $R^5$, $R^6$ and $R^7$ are as defined above (hereinafter referred to as the compound (14)) with the compound (7).

The reaction is carried out in the presence of a base or in the presence or the absence of a solvent. Examples of the solvent used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitrites such as acetonitrile; aprotic polar solvents such as N,N-dimethylformamide, N-methylpyrrolidone, 1,3-dimethyl-2-imidadzolidinone, and dimethyl sulfoxide; and a mixture thereof.

The amount of the compound (7) used in the reaction is usually from 0.5 to 2 mol per mol of the compound (14).

Examples of the base used in the reaction include nitrogen-containing heterocyclic compounds such as pyridine, picoline, 2,6-lutidine, 1,8-diazabicyclo[5,4,0]7-undecene (DBU), and 1,5-diazabicyclo[4,3,0] 5-nonene (DBN); tertiary amines such as triethylamine, and N,N-diisopropylethylamine; and inorganic bases such as potassium carbonate, and sodium hydride. The amount of the base when the reaction is carried out in the presence of the base is usually 1 mol or more per mol of the compound (14).

The reaction temperature is usually from 50 to 150° C. and the reaction time is usually from 1 to 24 hours.

After completion of the reaction, the compound (9) can be isolated by pouring the reaction mixture into water and extracting the mixture with an organic solvent, or collecting a deposited precipitate by filtration. The isolated compound (9) may be further purified, for example, by recrystallization, or chromatography.

The compound (9) can be produced by reacting a compound represented by the formula (15):

[Chemical Formula 20]

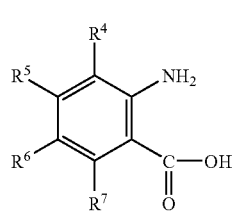

(15)

wherein $R^4$, $R^5$, $R^6$ and $R^7$ are as defined above (hereinafter referred to as the compound (15)) with the compound (7).

The reaction is carried out in the presence or the absence of a solvent. Examples of the solvent used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitrites such as acetonitrile; aprotic polar solvents such as N,N-dimethylformamide, N-methylpyrrolidone, 1,3-dimethyl-2-imidadzolidinone, and dimethyl sulfoxide; and a mixture thereof.

The process comprises the following (step 5-1) and (step 5-2).

(Step 5-1)

The step is carried out by reacting the compound (15) with the compound (7) in the presence of a base.

The amount of the compound (7) used in this step is usually 1 mol or more per mol of the compound (15). Examples of the base used in this step include nitrogen-containing heterocyclic compounds such as pyridine, picoline, 2,6-lutidine, 1,8-diazabicyclo[5,4,0]7-undecene (DBU), and 1,5-diazabicyclo[4,3,0]5-nonene (DBN); tertiary amines such as triethylamine, and N,N-diisopropylethylamine; and inorganic bases such as potassium carbonate, and sodium hydride. The amount of the base used is usually 1 mol or more per mol of the compound (15).

The reaction temperature of the step is usually from 0 to 50° C. and the reaction time is usually from 0.1 to 24 hours.

After completion of the step, the reaction mixture is used as it is for the following (step 5-2).

(Step 5-2)

The step is carried out by reacting the reaction mixture in the (step 5-1) with a sulfonyl halide in the presence of a base.

Examples of the sulfonyl halide used in this step include methanesulfonyl chloride, p-toluenesulfonyl chloride, and trifluoromethanesulfonyl chloride. The amount of the sulfonyl halide used in this step is usually from 1 mol or more per mol of the compound (15) used in the (step 5-1).

Examples of the base used in this step include the same bases as those described with respect to the (step 5-1) and usually include the same bases as those described with respect to the (step 5-1). The amount of the base used is usually 1 mol or more per mol of the compound (15) used in the (step 5-1).

The reaction temperature of the step is usually from 0 to 50° C. and the reaction time is usually from 0.1 to 24 hours.

After completion of this step, the compound (9) can be isolated by pouring the reaction mixture into water, followed by conventional extraction with an organic solvent. The isolated compound (9) may be further purified, for example, by recrystallization, or chromatography.

The compound (11) can be produced by reacting the compound (12) with a halogenating agent.

The reaction is carried out in the presence or the absence of a solvent. Examples of the solvent used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methylpyrrolidone, 1,3-dimethyl-2-imidazolidinone, and dimethyl sulfoxide; and a mixture thereof.

Examples of the halogenating agent used in the reaction include thionyl chloride, thionyl bromide, phosphorus oxychloride, phosphorus oxybromide, phosphorus pentachloride, oxalyl chloride and phosgene.

The amount of the halogenating agent used in the reaction is usually 1 mol or more per mol of the compound (12).

The reaction temperature is usually from 0° C. to 150° C. and the reaction time is usually from 0.1 to 24 hours.

After completion of the reaction, the compound (11) can be isolated by collecting a precipitate deposited in the reaction mixture by filtration, or extracting the reaction mixture with an organic solvent. The isolated compound (11) may be usually used in the next step as it is. If necessary, it may be further purified, for example, by recrystallization, or chromatography.

The compound (12) can be produced by reacting a compound represented by the formula (16):

[Chemical Formula 21]

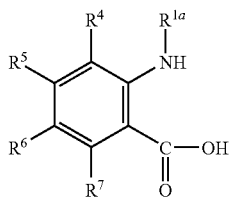

(16)

wherein $R^{1a}$, $R^4$, $R^5$, $R^6$ and $R^7$ are as defined above (hereinafter referred to as the compound (16)) with the compound (7).

The reaction is carried out in the presence or the absence of a solvent. Examples of the solvent used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methylpyrrolidone, 1,3-dimethyl-2-imidadzolidinone, and dimethyl sulfoxide; and a mixture thereof.

The amount of the compound (7) used in the reaction is usually 1 mol or more per mol of the compound (16).

The reaction is carried out in the presence of a base. Examples of the based used include nitrogen-containing heterocyclic compounds such as pyridine, picoline, 2,6-lutidine, 1,8-diazabicyclo[5,4,0]7-undecene (DBU), and 1,5-diazabicyclo[4,3,0]5-nonene (DBN); tertiary amines such as triethylamine, and N,N-diisopropylethylamine; and inorganic bases such as potassium carbonate, and sodium hydride. The amount of the base used is usually 1 mol or more per mol of the compound (16).

The reaction temperature of the step is usually from 0 to 50° C. and the reaction time is usually from 0.1 to 24 hours.

After completion of the reaction, the compound (12) can be isolated by pouring the reaction mixture into water and extracting the mixture with an organic solvent, or collecting a deposited precipitate by filtration. The isolated compound (12) may be further purified, for example, by recrystallization, or chromatography.

The compound (6) can be produced by reacting a compound represented by the formula (17):

[Chemical Formula 22]

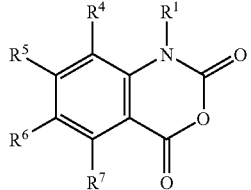

(17)

wherein $R^1$, $R^4$, $R^5$, $R^6$ and $R^7$ are as defined above (hereinafter referred to as the compound (17)) with the compound (10).

The reaction is carried out in the presence or the absence of a solvent. Examples of the solvent used in the reaction include ethers such as 1,4-dioxane, diethylether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methylpyrrolidone, 1,3-dimethyl-2-imidazolidinone, and dimethyl sulfoxide; alcohols such as methanol, ethanol, and isopropyl alcohol; and a mixture thereof.

The amount of the compound (10) used in the reaction is usually 1 mol or more per mol of the compound (17).

The reaction temperature is usually from −20 to 150° C. and the reaction time is usually from 0.1 to 24 hours.

After completion of the reaction, the compound (6) can be isolated by pouring the reaction mixture into water and extracting the mixture with an organic solvent, or collecting a deposited precipitate by filtration. The isolated compound (6) may be further purified, for example, by recrystallization, or chromatography.

The compound (6) can be produced according to the following scheme:

[Chemical Formula 23]

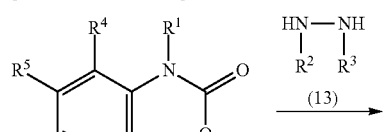

(17)

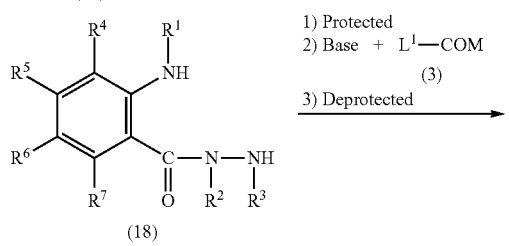

(18)

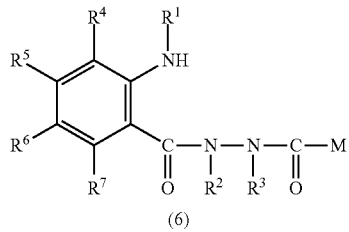

(6)

wherein $L^1$, $R^1$, $R^2$, $R^3$, $R^4$, $R^5$, $R^6$, $R^7$ and M are as defined above.

Compound (17)→Compound (18)

The amount of the compound (13) is usually 1 mol per mol of the compound (17).

The reaction is usually carried out in the presence of a solvent, and examples of the solvent include ethers such as 1,4-dioxane, diethylether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitrites such as acetonitrile; aprotic polar solvents such as N,N-dimethylformamide, N-methylpyrrolidone, 1,3-dimethyl-2-imidazolidinone, and dimethyl sulfoxide; alcohols such as methanol, ethanol, and isopropyl alcohol; and a mixture thereof.

Compound (18)→Compound (6)

1) The amino group (—$NHR^1$ group) on the benzene ring of the compound (18) can be protected with a suitable protecting group (e.g. N-benzylidene group, N-(1-methyl)ethylidene group, and benzyloxycarbonyl group) described in Greene's Protective Groups in Organic Synthesis (WILEY) etc., if necessary.
2) The amount of the compound (3) used is usually 1 mol per mol of the compound (18) or a derivative thereof in which the amino group is protected. Examples of the base used in the reaction include metal carbonates such as potassium carbonate.
3) The compound (6) in which the amino group is protected can be deprotected under known conditions.

Among the compound (6), a compound represented by the formula (6-ii) can be produced according to the following scheme:

[Chemical Formula 24]

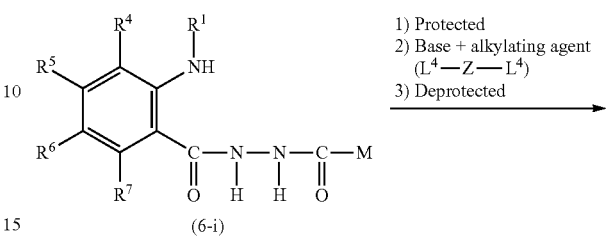

(6-i)

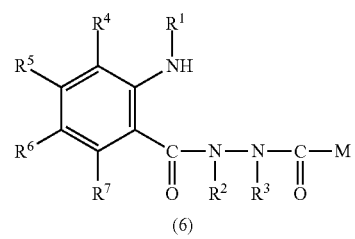

(6)

wherein $L^4$ represents a leaving group (e.g., a halogen atom, a methanesulfonyloxy group, a p-toluenesulfonyloxy group, and the like) and $R^1$, $R^4$, $R^5$, $R^6$, $R^7$, Z and M are as defined above.

1) The amino group (—$NHR^1$ group) on the benzene ring of the compound (6-i) can be protected with a suitable protecting group (e.g. N-benzylidene group, N-(1-methyl)ethylidene group, and benzyloxycarbonyl group) described in Greene's Protective Groups in Organic Synthesis (WILEY) etc., if necessary.
2) The amount of the alkylating agent used is usually 2 mol per mol of the compound (6-i) or a derivative thereof in which the amino group is protected. Examples of the base used in the reaction include metal carbonates such as potassium carbonate.
3) The compound (6-ii) in which the amino group is protected can be deprotected under known conditions.

The compounds (3) and (13) are known compounds, or can be produced from known compounds according to known methods (see, for example, Organic Functional Group Preparations, 2nd edition, Vol. 1, chapter 12, P. 359-376, Stanley R. Sandler, Wolf Karo, or Organic Functional Group Preparations, 2nd edition, Vol. 1, chapter 14, P. 434-465, Stanley R. Sandler, Wolf Karo.).

The compound (10) can be produced according to a method, for example, shown in the following scheme:

[Chemical Formula 25]

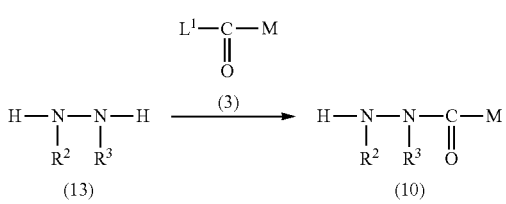

wherein $L^1$, $R^2$, $R^3$ and M are as defined above.

The compound (15) can be produced according to a method, for example, shown in the following scheme:

[Chemical Formula 26]

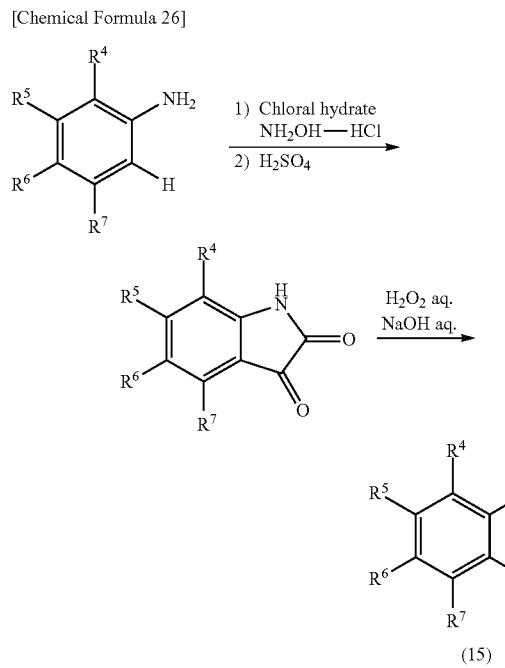

wherein $R^4$, $R^5$, $R^6$ and $R^7$ are as defined above.

The compounds (14), (16) and (17) can be produced according to a method, for example, shown in the following scheme:

[Chemical Formula 27]

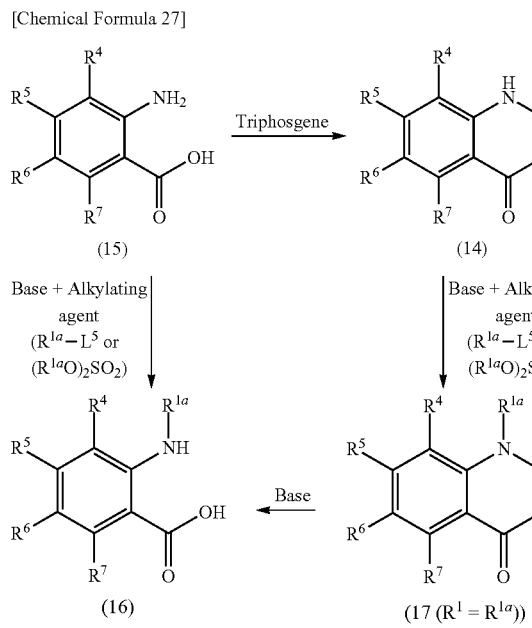

wherein $R^{1a}$, $R^4$, $R^5$, $R^6$ and $R^7$ are as defined above and $L^5$ represents a leaving group (e.g., a halogen atom, a methanesulfonyloxy group, a p-toluenesulfonyloxy group, and the like).

Among the compound (8), a compound represented by the formula (8-i):

[Chemical Formula 28]

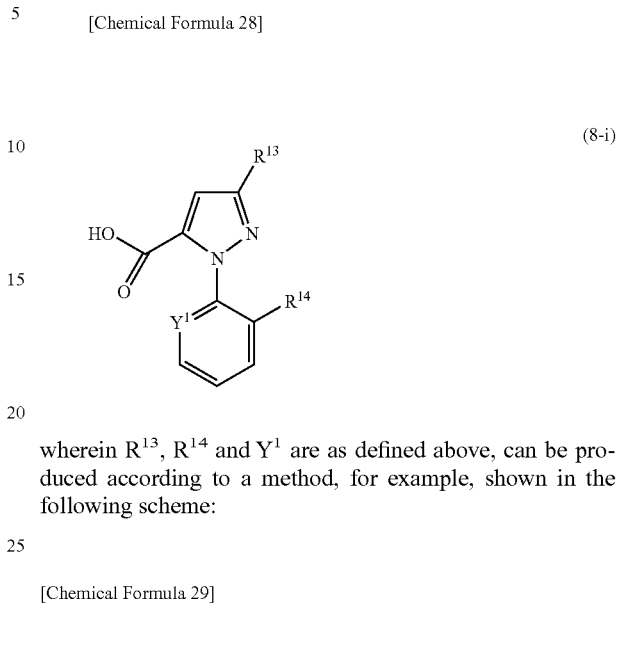

wherein $R^{13}$, $R^{14}$ and $Y^1$ are as defined above, can be produced according to a method, for example, shown in the following scheme:

[Chemical Formula 29]

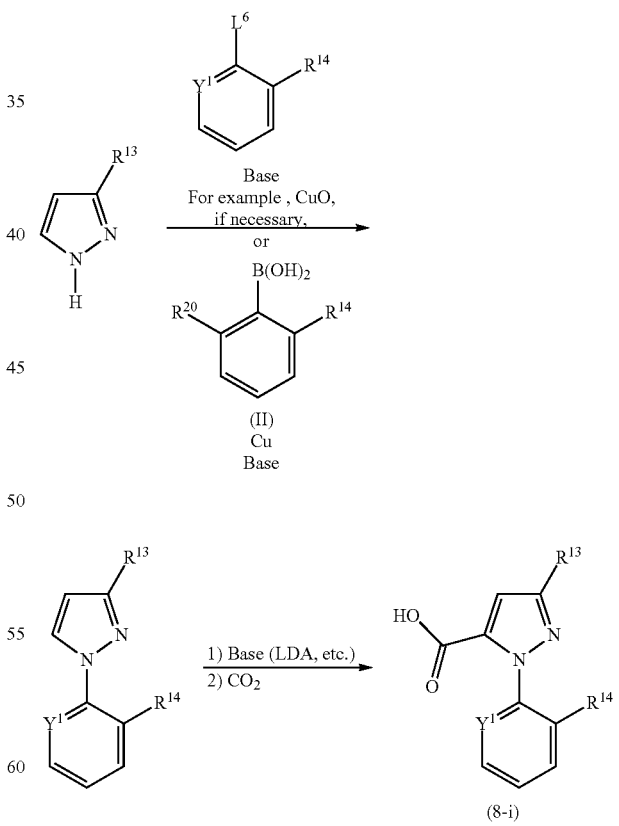

wherein $R^{14}$, $R^{13}$, $R^{20}$ and $Y^1$ are as defined above and $L^6$ represents a leaving group (e.g., a halogen atom, methylsulfonyl group, and the like).

Among the compound (8), compounds represented by the formula (8-ii) and the formula (8-iii):

[Chemical Formula 30]

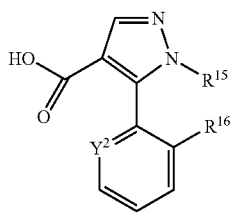
(8-ii)

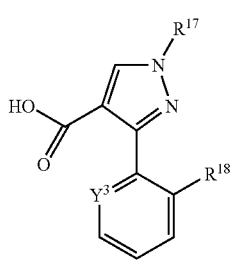
(8-iii)

wherein $R^{15}$, $R^{16}$, $R^{17}$, $R^{18}$, $Y^2$ and $Y^3$ are as defined above, can be produced according to a method, for example, shown in the following scheme:

[Chemical Formula 31]

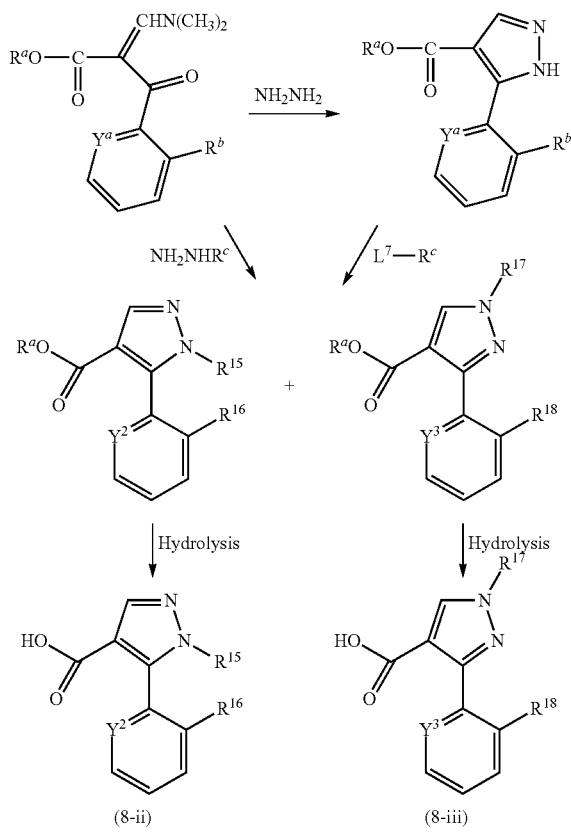

wherein $R^{15}$, $R^{16}$, $R^{17}$, $R^{18}$, $Y^2$ and $Y^3$ are as defined above, $R^a$ represents a methyl group or an ethyl group, $Y^a$ is as defined in $Y^2$ or $Y^3$, $R^b$ is as defined in $R^{16}$ or $R^{18}$, $R^c$ is as defined in $R^{15}$ or $R^{17}$, and $L^7$ represents a leaving group (e.g., a halogen atom, methanesulfonyloxy group, p-toluenesulfonyloxy group, and the like).

Among the compound (8), a compound represented by the formula (8-iv):

[Chemical Formula 32]

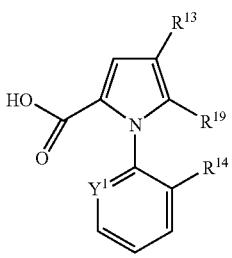
(8-iv)

wherein $R^{13}$, $R^{14}$, $R^{19}$ and $Y^1$ are as defined above, can be produced according to a method, for example, shown in the following scheme:

[Chemical Formula 33]

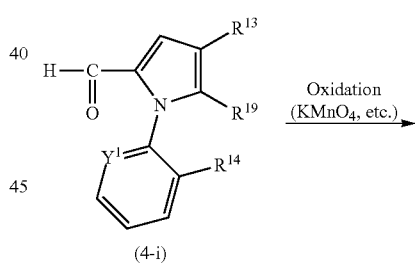

(4-i)

Oxidation
(KMnO$_4$, etc.)

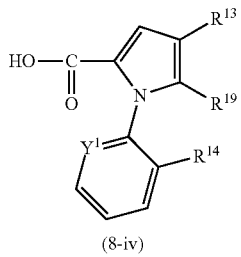
(8-iv)

wherein $R^{13}$, $R^{14}$, $R^{19}$ and $Y^1$ are as defined above.

Among the compound (4), a compound (4-i) can be produced according to a process, for example, shown in the following scheme:

[Chemical Formula 34]

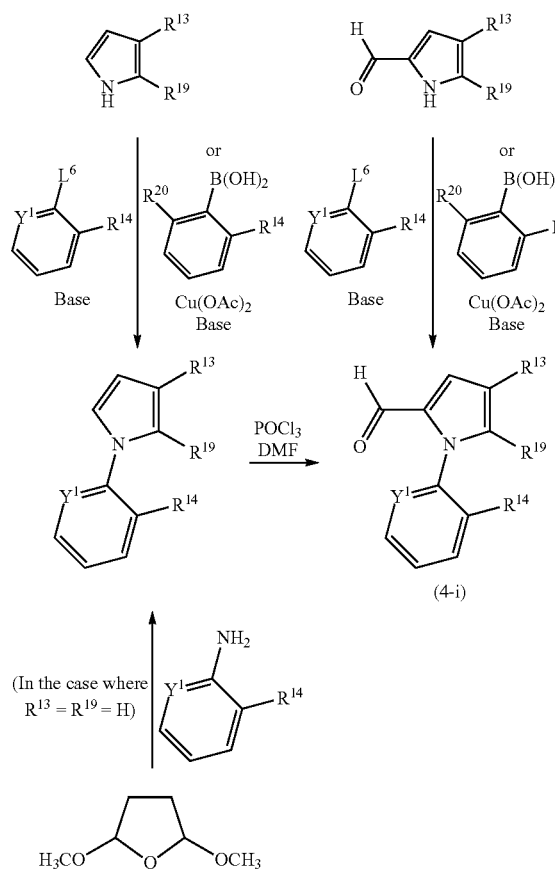

wherein $R^{13}$, $R^{14}$, $R^{19}$, $R^{20}$, $Y^1$ and $L^6$ are as defined above.

Among the compound (4), compounds represented by the formula (4-ii), the formula (4-iii) and the formula (4-iv):

[Chemical Formula 35]

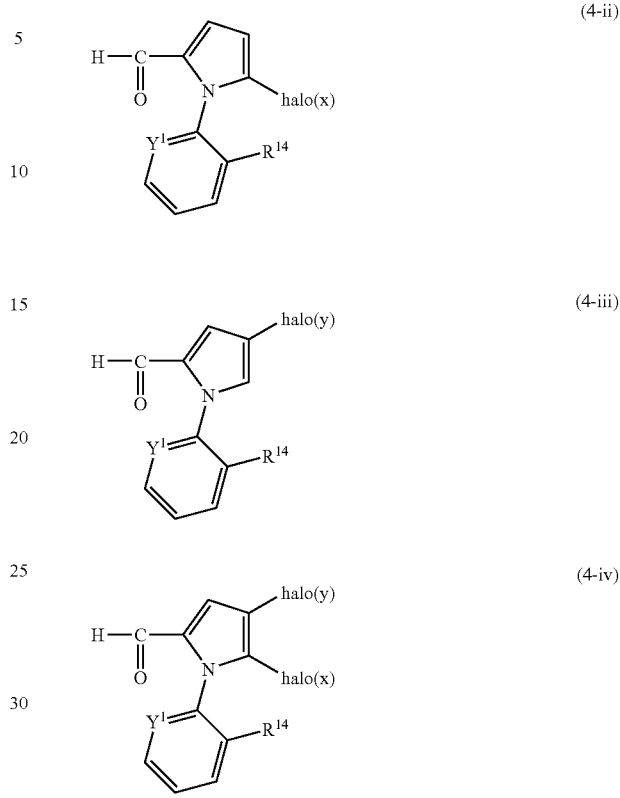

wherein $R^{14}$ and $Y^1$ are as defined above, and halo(x) and halo(y) each independently represents a halogen atom can be produced according to a method, for example, shown in the following scheme:

[Chemical Formula 36]

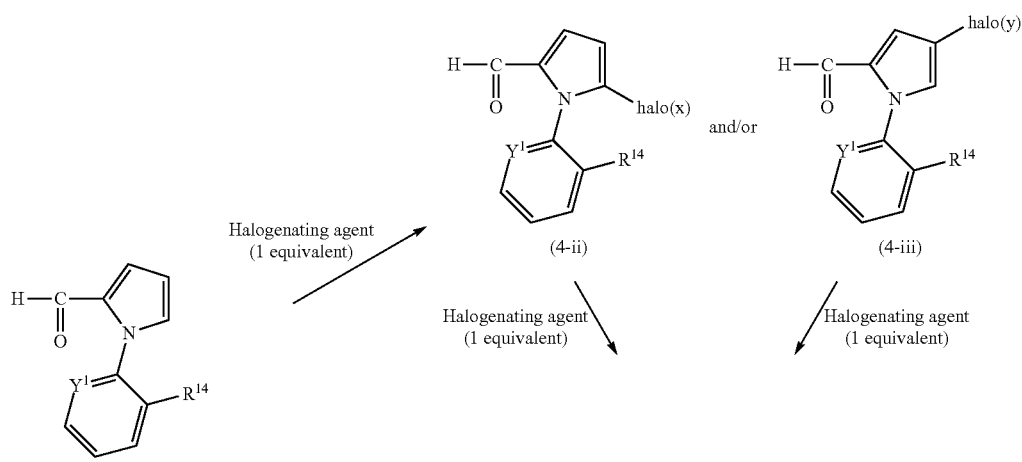

-continued

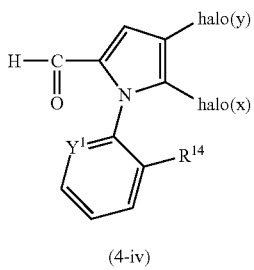

(4-iv)

wherein $R^{14}$, $Y^1$, halo(x) and halo(y) are as defined above.

Among the compound (4), a compound represented by the formula (4-v):

[Chemical Formula 37]

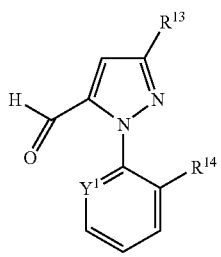

(X-v)

wherein $R^{13}$, $R^{14}$ and $Y^1$ are as defined above, can be produced according to a process, for example, shown in the following scheme:

[Chemical Formula 38]

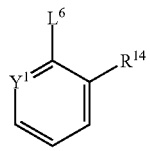

1) For example, 3-($R^{13}$)-substituted-1H-pirazol, base and, if necessary, CuO
2) LDA  →  HC(=O)—$L^8$

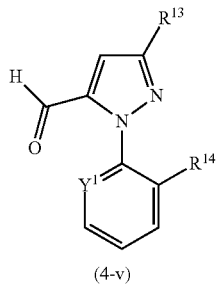

(4-v)

wherein $L^6$ represents a leaving group (e.g., a halogen atom, methylsulfonyl group, and the like), $L^8$ represents a leaving group (e.g., a methoxy group, an ethoxy group, an N,N-dimethylamino group, and the like) and $R^{13}$, $R^{14}$ and $Y^1$ are as defined above, and

[Chemical Formula 39]

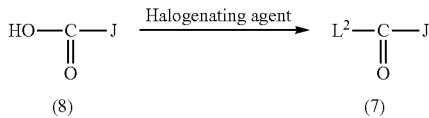

wherein $L^2$ and J are as defined above.

The compounds obtained by the processes described above can be isolated and purified by a conventional method such as grinding, powdering, recrystallization, column chromatography, high performance column chromatography (HPLC), medium pressure preparative HPLC, desalting resin column chromatography, and re-precipitation.

The present compound can be isolated in the form of, for example, a salt (a salt obtained by reacting the present compound with an acid or a base), or a solvate (e.g., a hydrate) according to particular conditions, and the compounds in these forms are also included in the present invention.

The present compound can exist as a tautomer, and the tautomer is also included in the present compound.

Hereinafter, specific examples of the present compound are shown.

A compound represented by the formula (A-1):

[Chemical Formula 40]

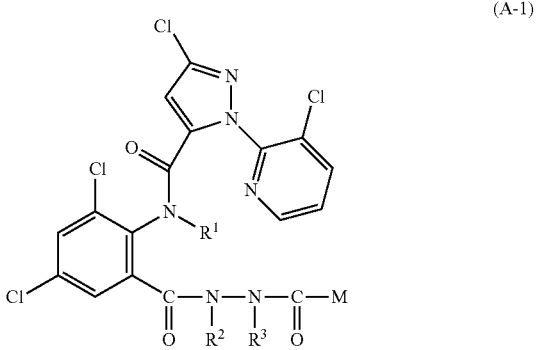

(A-1)

wherein $R^1$, $R^2$, $R^3$ and M represent the combinations described in Table 1 to Table 9.

TABLE 1

| $R^1$ | $R^2$ | $R^3$ | M |
|---|---|---|---|
| H | —$CH_2CH_2CH_2$— | | H |
| H | —$CH_2CH_2CH_2CH_2$— | | H |
| H | —$CH_2CH_2CH_2CH_2CH_2$— | | H |
| H | —$CH_2CH=CHCH_2$— | | H |
| H | —$CH_2CH_2OCH_2CH_2$— | | H |
| H | —$CH_2CH_2SCH_2CH_2$— | | H |
| H | —$CH_2CH_2S(=O)CH_2CH_2$— | | H |
| H | —$CH_2CH_2S(=O)_2CH_2CH_2$— | | H |
| H | —$CH_2CH_2N(CH_3)CH_2CH_2$— | | H |
| $CH_3$ | —$CH_2CH_2CH_2$— | | H |
| $CH_3$ | —$CH_2CH_2CH_2CH_2$— | | H |
| $CH_3$ | —$CH_2CH_2CH_2CH_2CH_2$— | | H |
| $CH_3$ | —$CH_2CH=CHCH_2$— | | H |
| $CH_3$ | —$CH_2CH_2OCH_2CH_2$— | | H |
| $CH_3$ | —$CH_2CH_2SCH_2CH_2$— | | H |

TABLE 1-continued

| R¹ | R² R³ | M |
|---|---|---|
| CH₃ | —CH₂CH₂S(=O)CH₂CH₂— | H |
| CH₃ | —CH₂CH₂S(=O)₂CH₂CH₂— | H |
| CH₃ | —CH₂CH₂N(CH₃)CH₂CH₂— | H |

TABLE 2

| R¹ | R² R³ | M |
|---|---|---|
| H | —CH₂CH₂CH₂— | OCH₃ |
| H | —CH₂CH₂CH₂CH₂— | OCH₃ |
| H | —CH₂CH₂CH₂CH₂CH₂— | OCH₃ |
| H | —CH₂CH=CHCH₂— | OCH₃ |
| H | —CH₂CH₂OCH₂CH₂— | OCH₃ |
| H | —CH₂CH₂SCH₂CH₂— | OCH₃ |
| H | —CH₂CH₂S(=O)CH₂CH₂— | OCH₃ |
| H | —CH₂CH₂S(=O)₂CH₂CH₂— | OCH₃ |
| H | —CH₂CH₂N(CH₃)CH₂CH₂— | OCH₃ |
| CH₃ | —CH₂CH₂CH₂— | OCH₃ |
| CH₃ | —CH₂CH₂CH₂CH₂— | OCH₃ |
| CH₃ | —CH₂CH₂CH₂CH₂CH₂— | OCH₃ |
| CH₃ | —CH₂CH=CHCH₂— | OCH₃ |
| CH₃ | —CH₂CH₂OCH₂CH₂— | OCH₃ |
| CH₃ | —CH₂CH₂SCH₂CH₂— | OCH₃ |
| CH₃ | —CH₂CH₂S(=O)CH₂CH₂— | OCH₃ |
| CH₃ | —CH₂CH₂S(=O)₂CH₂CH₂— | OCH₃ |
| CH₃ | —CH₂CH₂N(CH₃)CH₂CH₂— | OCH₃ |

TABLE 3

| R¹ | R² R³ | M |
|---|---|---|
| H | —CH₂CH₂CH₂— | N(CH₃)₂ |
| H | —CH₂CH₂CH₂CH₂— | N(CH₃)₂ |
| H | —CH₂CH₂CH₂CH₂CH₂— | N(CH₃)₂ |
| H | —CH₂CH=CHCH₂— | N(CH₃)₂ |
| H | —CH₂CH₂OCH₂CH₂— | N(CH₃)₂ |
| H | —CH₂CH₂SCH₂CH₂— | N(CH₃)₂ |
| H | —CH₂CH₂S(=O)CH₂CH₂— | N(CH₃)₂ |
| H | —CH₂CH₂S(=O)₂CH₂CH₂— | N(CH₃)₂ |
| H | —CH₂CH₂N(CH₃)CH₂CH₂— | N(CH₃)₂ |
| CH₃ | —CH₂CH₂CH₂— | N(CH₃)₂ |
| CH₃ | —CH₂CH₂CH₂CH₂— | N(CH₃)₂ |
| CH₃ | —CH₂CH₂CH₂CH₂CH₂— | N(CH₃)₂ |
| CH₃ | —CH₂CH=CHCH₂— | N(CH₃)₂ |
| CH₃ | —CH₂CH₂OCH₂CH₂— | N(CH₃)₂ |
| CH₃ | —CH₂CH₂SCH₂CH₂— | N(CH₃)₂ |
| CH₃ | —CH₂CH₂S(=O)CH₂CH₂— | N(CH₃)₂ |
| CH₃ | —CH₂CH₂S(=O)₂CH₂CH₂— | N(CH₃)₂ |
| CH₃ | —CH₂CH₂N(CH₃)CH₂CH₂— | N(CH₃)₂ |

TABLE 4

| R¹ | R² R³ | M |
|---|---|---|
| H | —CH₂CH₂CH₂— | CH₃ |
| H | —CH₂CH₂CH₂CH₂— | CH₃ |
| H | —CH₂CH₂CH₂CH₂CH₂— | CH₃ |
| H | —CH₂CH=CHCH₂— | CH₃ |
| H | —CH₂CH₂OCH₂CH₂— | CH₃ |
| H | —CH₂CH₂SCH₂CH₂— | CH₃ |
| H | —CH₂CH₂S(=O)CH₂CH₂— | CH₃ |
| H | —CH₂CH₂S(=O)₂CH₂CH₂— | CH₃ |
| H | —CH₂CH₂N(CH₃)CH₂CH₂— | CH₃ |
| CH₃ | —CH₂CH₂CH₂— | CH₃ |
| CH₃ | —CH₂CH₂CH₂CH₂— | CH₃ |
| CH₃ | —CH₂CH₂CH₂CH₂CH₂— | CH₃ |
| CH₃ | —CH₂CH=CHCH₂— | CH₃ |
| CH₃ | —CH₂CH₂OCH₂CH₂— | CH₃ |
| CH₃ | —CH₂CH₂SCH₂CH₂— | CH₃ |
| CH₃ | —CH₂CH₂S(=O)CH₂CH₂— | CH₃ |

TABLE 4-continued

| R¹ | R² R³ | M |
|---|---|---|
| CH₃ | —CH₂CH₂S(=O)₂CH₂CH₂— | CH₃ |
| CH₃ | —CH₂CH₂N(CH₃)CH₂CH₂— | CH₃ |

TABLE 5

| R¹ | R² R³ | M |
|---|---|---|
| H | —CH₂CH₂CH₂— | OCH₂CH₃ |
| H | —CH₂CH₂CH₂CH₂— | OCH₂CH₃ |
| H | —CH₂CH₂CH₂CH₂CH₂— | OCH₂CH₃ |
| H | —CH₂CH=CHCH₂— | OCH₂CH₃ |
| H | —CH₂CH₂OCH₂CH₂— | OCH₂CH₃ |
| H | —CH₂CH₂SCH₂CH₂— | OCH₂CH₃ |
| H | —CH₂CH₂S(=O)CH₂CH₂— | OCH₂CH₃ |
| H | —CH₂CH₂S(=O)₂CH₂CH₂— | OCH₂CH₃ |
| H | —CH₂CH₂N(CH₃)CH₂CH₂— | OCH₂CH₃ |
| CH₃ | —CH₂CH₂CH₂— | OCH₂CH₃ |
| CH₃ | —CH₂CH₂CH₂CH₂— | OCH₂CH₃ |
| CH₃ | —CH₂CH₂CH₂CH₂CH₂— | OCH₂CH₃ |
| CH₃ | —CH₂CH=CHCH₂— | OCH₂CH₃ |
| CH₃ | —CH₂CH₂OCH₂CH₂— | OCH₂CH₃ |
| CH₃ | —CH₂CH₂SCH₂CH₂— | OCH₂CH₃ |
| CH₃ | —CH₂CH₂S(=O)CH₂CH₂— | OCH₂CH₃ |
| CH₃ | —CH₂CH₂S(=O)₂CH₂CH₂— | OCH₂CH₃ |
| CH₃ | —CH₂CH₂N(CH₃)CH₂CH₂— | OCH₂CH₃ |

TABLE 6

| R¹ | R² R³ | M |
|---|---|---|
| H | —CH₂CH(CH₃)CH₂— | H |
| H | —CH₂C(CH₃)₂CH₂— | H |
| H | —CH(CH₃)CH₂CH₂— | H |
| H | —CH₂CH₂CH(CH₃)— | H |
| H | —CH(CH₃)CH₂CH(CH₃)— | H |
| H | —CH₂CHClCH₂— | H |
| H | —CH₂CHBrCH₂— | H |
| H | —CH₂CH(COOCH₃)CH₂— | H |
| H | —CH₂CH(COOCH₂CH₃)CH₂— | H |
| H | —CH(COOCH₃)CH₂CH₂— | H |
| H | —CH(COOCH₂CH₃)CH₂CH₂— | H |
| H | —CH₂CH₂CH(COOCH₃)— | H |
| H | —CH₂CH₂CH(COOCH₂CH₃)— | H |
| H | —CH(COOCH₃)CH₂CH(COOCH₃)— | H |
| H | —CH(COOCH₂CH₃)CH₂CH(COOCH₂CH₃)— | H |
| H | —CH₂CH(CH₃)CH₂— | H |
| H | —CH₂CH(CH₃)CH(CH₃)— | H |
| H | —CH₂C(CH₃)₂CH₂— | H |
| H | —CH₂CH₂C(CH₃)₂CH₂— | H |
| H | —CH(CH₃)CH₂CH₂CH₂— | H |
| H | —CH(CH₃)CH₂CH(CH₃)— | H |
| H | —CH(CH₃)CH₂CH₂CH(CH₃)— | H |
| H | —CH(COOCH₃)CH₂CH₂CH₂— | H |
| H | —CH(COOCH₂CH₃)CH₂CH₂CH₂— | H |
| H | —CH₂CH₂CH₂CH(COOCH₃)— | H |
| H | —CH₂CH₂CH₂CH(COOCH₂CH₃)— | H |
| H | —CH(COOCH₃)CH₂CH₂CH(COOCH₃)— | H |
| H | —CH(COOCH₂CH₃)CH₂CH₂CH(COOCH₂CH₃)— | H |

TABLE 7

| R¹ | R² R³ | M |
|---|---|---|
| H | —CH₂CH₂NHCH₂CH₂— | H |
| H | —CH₂CH₂N(CHO)CH₂CH₂— | H |
| H | —CH₂CH₂N(COCH₃)CH₂CH₂— | H |
| H | —CH₂CH₂N(COOCH₃)CH₂CH₂— | H |
| H | —CH₂CH₂N(COOCH₂CH₃)CH₂CH₂— | H |
| H | —CH₂CH₂C(=O)— | H |
| H | —CH(CH₃)CH₂C(=O)— | H |
| H | —C(=O)CH₂CH₂— | H |

TABLE 7-continued

| R¹ | R² | R³ | M |
|---|---|---|---|
| H | —C(=O)CH₂CH(CH₃)— | | H |
| H | —CH₂C(=O)CH₂— | | H |
| H | —CH₂CH₂CH₂C(=O)— | | H |
| H | —C(=O)CH₂CH₂CH₂— | | H |
| H | —CH₂NHCH₂— | | H |
| H | —CH₂N(CH₃)CH₂— | | H |
| H | —CH₂N(CHO)CH₂— | | H |
| H | —CH₂N(COCH₃)CH₂— | | H |
| H | —CH₂N(COOCH₃)CH₂— | | H |
| H | —CH₂N(COOCH₂CH₃)CH₂— | | H |

TABLE 8

| R¹ | R² | R³ | M |
|---|---|---|---|
| H | —CH₂CH(CH₃)CH₂— | | OCH₃ |
| H | —CH₂C(CH₃)₂CH₂— | | OCH₃ |
| H | —CH(CH₃)CH₂CH₂— | | OCH₃ |
| H | —CH₂CH₂CH(CH₃)— | | OCH₃ |
| H | —CH(CH₃)CH₂CH(CH₃)— | | OCH₃ |
| H | —CH₂CHClCH₂— | | OCH₃ |
| H | —CH₂CHBrCH₂— | | OCH₃ |
| H | —CH₂CH(COOCH₃)CH₂— | | OCH₃ |
| H | —CH₂CH(COOCH₂CH₃)CH₂— | | OCH₃ |
| H | —CH(COOCH₃)CH₂CH₂— | | OCH₃ |
| H | —CH(COOCH₂CH₃)CH₂CH₂— | | OCH₃ |
| H | —CH₂CH₂CH(COOCH₃)— | | OCH₃ |
| H | —CH₂CH₂CH(COOCH₂CH₃)— | | OCH₃ |
| H | —CH(COOCH₃)CH₂CH(COOCH₃)— | | OCH₃ |
| H | —CH(COOCH₂CH₃)CH₂CH(COOCH₂CH₃)— | | OCH₃ |
| H | —CH₂CH(CH₃)CH₂CH₂— | | OCH₃ |
| H | —CH₂CH₂CH(CH₃)CH₂— | | OCH₃ |
| H | —CH₂C(CH₃)₂CH₂CH₂— | | OCH₃ |
| H | —CH₂CH₂C(CH₃)₂CH₂— | | OCH₃ |
| H | —CH(CH₃)CH₂CH₂CH₂— | | OCH₃ |
| H | —CH₂CH₂CH₂CH(CH₃)— | | OCH₃ |
| H | —CH(CH₃)CH₂CH₂CH(CH₃)— | | OCH₃ |
| H | —CH(COOCH₃)CH₂CH₂CH₂— | | OCH₃ |
| H | —CH(COOCH₂CH₃)CH₂CH₂CH₂— | | OCH₃ |
| H | —CH₂CH₂CH₂CH(COOCH₃)— | | OCH₃ |
| H | —CH₂CH₂CH₂CH(COOCH₂CH₃)— | | OCH₃ |
| H | —CH(COOCH₃)CH₂CH₂CH(COOCH₃)— | | OCH₃ |
| H | —CH(COOCH₂CH₃)CH₂CH₂CH(COOCH₂CH₃)— | | OCH₃ |

TABLE 9

| R¹ | R² | R³ | M |
|---|---|---|---|
| H | —CH₂CH₂NHCH₂CH₂— | | OCH₃ |
| H | —CH₂CH₂N(CHO)CH₂CH₂— | | OCH₃ |
| H | —CH₂CH₂N(COCH₃)CH₂CH₂— | | OCH₃ |
| H | —CH₂CH₂N(COOCH₃)CH₂CH₂— | | OCH₃ |
| H | —CH₂CH₂N(COOCH₂CH₃)CH₂CH₂— | | OCH₃ |
| H | —CH₂CH₂C(=O)— | | OCH₃ |
| H | —CH(CH₃)CH₂C(=O)— | | OCH₃ |
| H | —C(=O)CH₂CH₂— | | OCH₃ |
| H | —C(=O)CH₂CH(CH₃)— | | OCH₃ |
| H | —CH₂C(=O)CH₂— | | OCH₃ |
| H | —CH₂CH₂CH₂C(=O)— | | OCH₃ |
| H | —C(=O)CH₂CH₂CH₂— | | H |
| H | —CH₂NHCH₂— | | OCH₃ |
| H | —CH₂N(CH₃)CH₂— | | OCH₃ |
| H | —CH₂N(CHO)CH₂— | | OCH₃ |
| H | —CH₂N(COCH₃)CH₂— | | OCH₃ |
| H | —CH₂N(COOCH₃)CH₂— | | OCH₃ |
| H | —CH₂N(COOCH₂CH₃)CH₂— | | OCH₃ |

A compound represented by the formula (A-2)

[Chemical Formula 41]

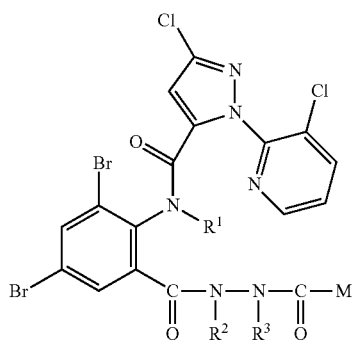

(A-2)

wherein R¹, R², R³ and M represent the combinations described in Table 1 to Table 9.

A compound represented by the formula (A-3):

[Chemical Formula 42]

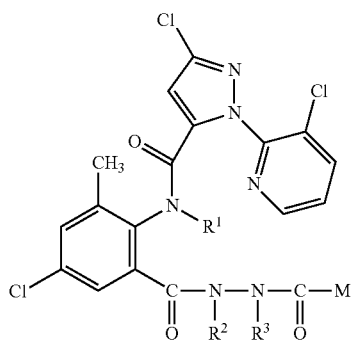

(A-3)

wherein R¹, R², R³ and M represent the combinations described in Table 1 to Table 9.

A compound represented by the formula (A-4):

[Chemical Formula 43]

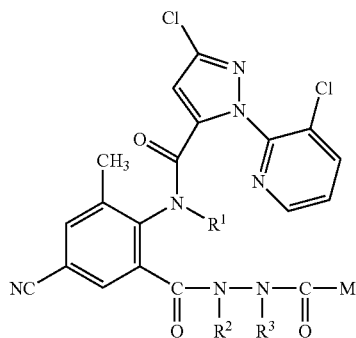

(A-4)

wherein R¹, R², R³ and M represent the combinations described in Table 1 to Table 9.

A compound represented by the formula (A-5):

[Chemical Formula 44]

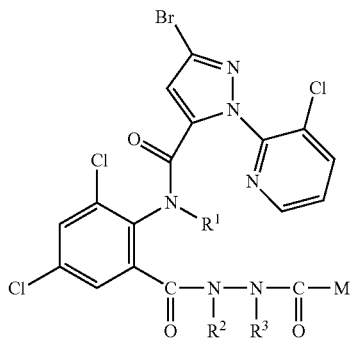
(A-5)

wherein $R^1$, $R^2$, $R^3$ and M represent the combinations described in Table 1 to Table 9.

A compound represented by the formula (A-6):

[Chemical Formula 45]

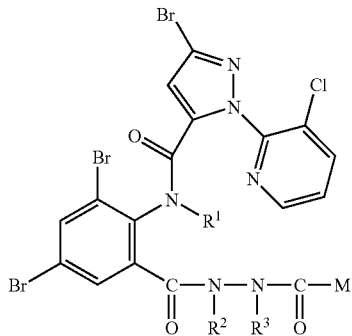
(A-6)

wherein $R^1$, $R^2$, $R^3$ and M represent the combinations described in Table 1 to Table 9.

A compound represented by the formula (A-7):

[Chemical Formula 46]

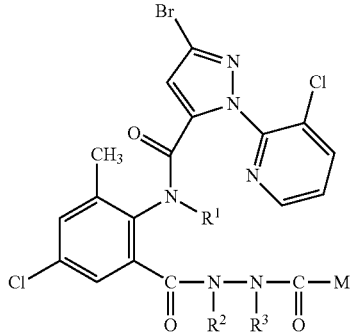
(A-7)

wherein $R^1$, $R^2$, $R^3$ and M represent the combinations described in Table 1 to Table 9.

A compound represented by the formula (A-8):

[Chemical Formula 47]

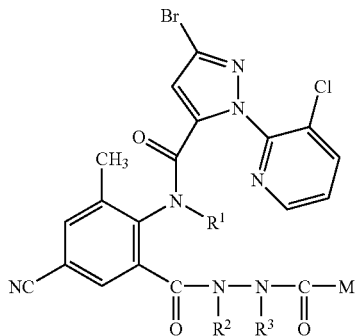
(A-8)

wherein $R^1$, $R^2$, $R^3$ and M represent the combinations described in Table 1 to Table 9.

A compound represented by the formula (A-9):

[Chemical Formula 48]

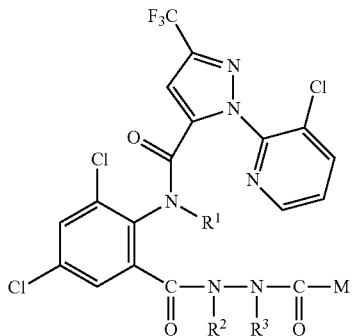
(A-9)

wherein $R^1$, $R^2$, $R^3$ and M represent the combinations described in Table 1 to Table 9.

A compound represented by the formula (A-10):

[Chemical Formula 49]

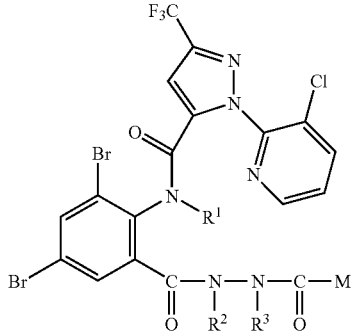
(A-10)

wherein $R^1$, $R^2$, $R^3$ and M represent the combinations described in Table 1 to Table 9.

A compound represented by the formula (A-11):

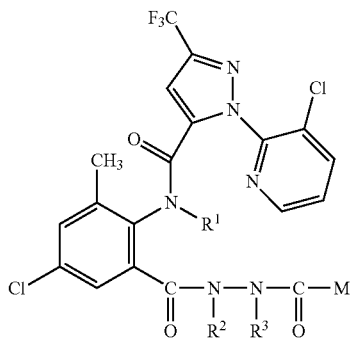

wherein $R^1$, $R^2$, $R^3$ and M represent the combinations described in Table 1 to Table 9.

A compound represented by the formula (A-12):

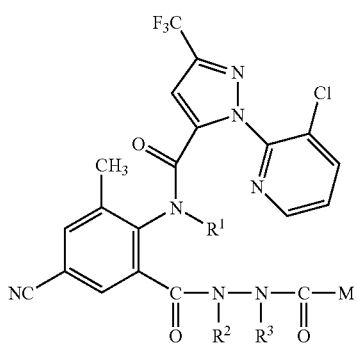

wherein $R^1$, $R^2$, $R^3$ and M represent the combinations described in Table 1 to Table 9.

A compound represented by the formula (A-13):

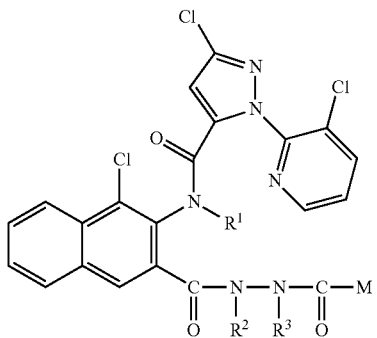

wherein $R^1$, $R^2$, $R^3$ and M represent the combinations described in Table 1 to Table 9.

A compound represented by the formula (A-14):

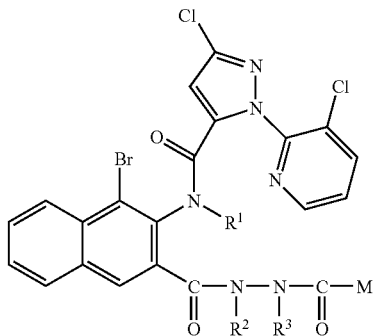

wherein $R^1$, $R^2$, $R^3$ and M represent the combinations described in Table 1 to Table 9.

A compound represented by the formula (A-15):

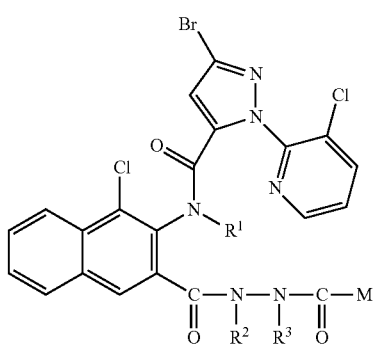

wherein $R^1$, $R^2$, $R^3$ and M represent the combinations described in Table 1 to Table 9.

A compound represented by the formula (A-16):

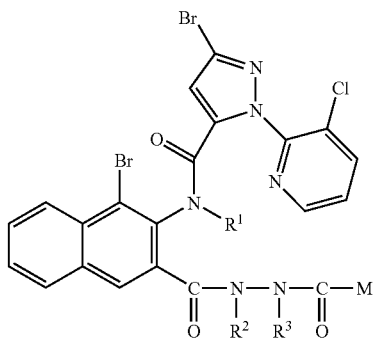

wherein $R^1$, $R^2$, $R^3$ and M represent the combinations described in Table 1 to Table 9.

A compound represented by the formula (A-17):

[Chemical Formula 56]

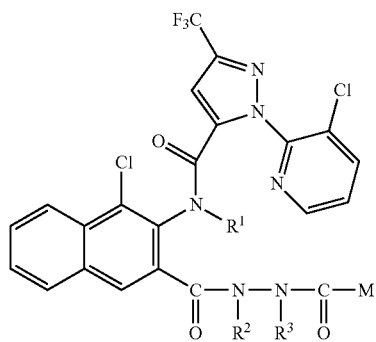

(A-17)

wherein R¹, R², R³ and M represent the combinations described in Table 1 to Table 9.

A compound represented by the formula (A-18):

[Chemical Formula 57]

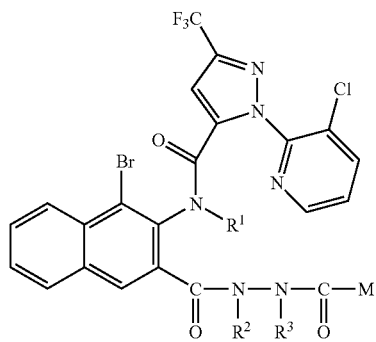

(A-18)

wherein R¹, R², R³ and M represent the combinations described in Table 1 to Table 9.

A compound represented by the formula (A-19):

[Chemical Formula 58]

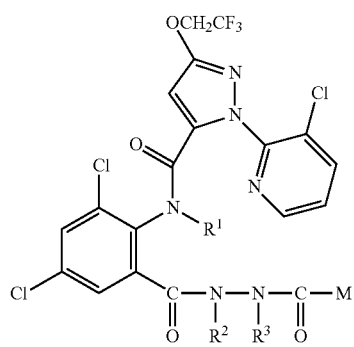

(A-19)

wherein R¹, R², R³ and M represent the combinations described in Table 1 to Table 9.

A compound represented by the formula (A-20):

[Chemical Formula 59]

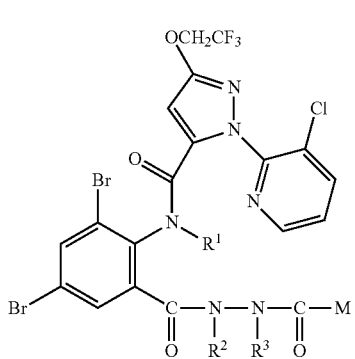

(A-20)

wherein R¹, R², R³ and M represent the combinations described in Table 1 to Table 9.

A compound represented by the formula (A-21):

[Chemical Formula 60]

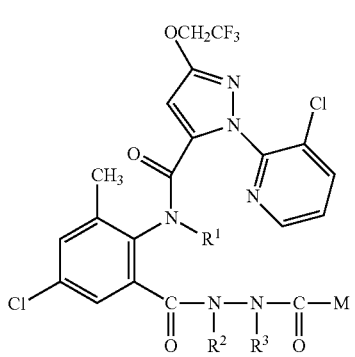

(A-21)

wherein R¹, R², R³ and M represent the combinations described in Table 1 to Table 9.

A compound represented by the formula (A-22):

[Chemical Formula 61]

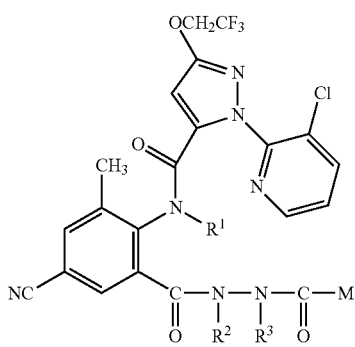

(A-22)

wherein R¹, R², R³ and M represent the combinations described in Table 1 to Table 9.

A compound represented by the formula (A-23):

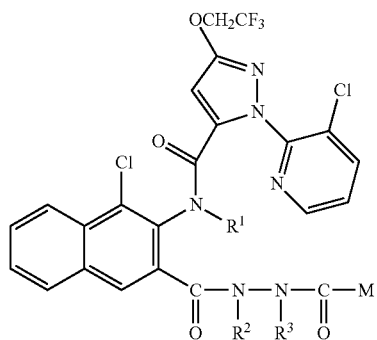
(A-23)

wherein $R^1$, $R^2$, $R^3$ and M represent the combinations described in Table 1 to Table 9.

A compound represented by the formula (A-24):

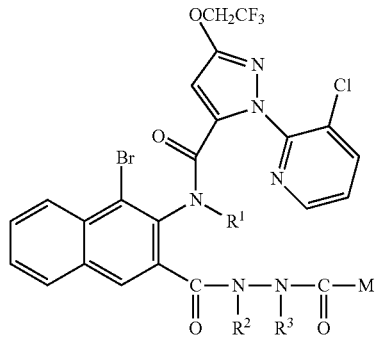
(A-24)

wherein $R^1$, $R^2$, $R^3$, and M represent the combinations described in Table 1 to Table 9.

A compound represented by the formula (A-25):

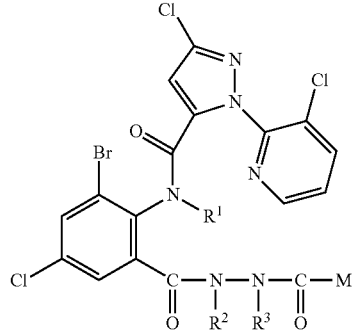
(A-25)

wherein $R^1$, $R^2$, $R^3$ and M represent the combinations described in Table 1 to Table 9.

A compound represented by the formula (A-26):

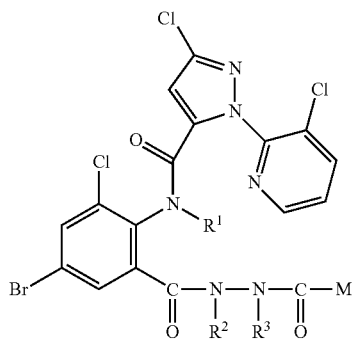
(A-26)

wherein $R^1$, $R^2$, $R^3$ and M represent the combinations described in Table 1 to Table 9.

A compound represented by the formula (A-27):

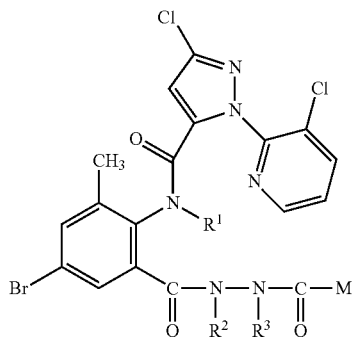
(A-27)

wherein $R^1$, $R^2$, $R^3$ and M represent the combinations described in Table 1 to Table 9.

A compound represented by the formula (A-28):

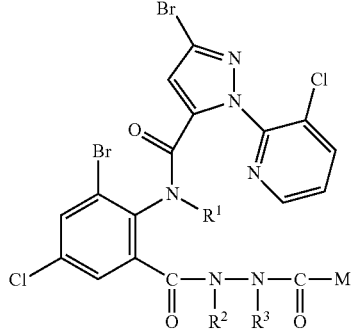
(A-28)

wherein $R^1$, $R^2$, $R^3$ and M represent the combinations described in Table 1 to Table 9.

A compound represented by the formula (A-29):

[Chemical Formula 68]

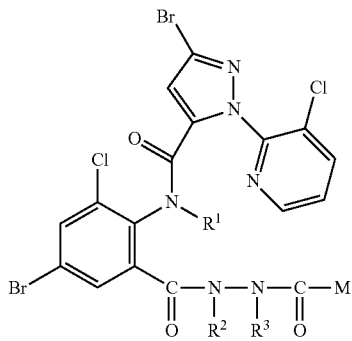
(A-29)

wherein R¹, R², R³ and M represent the combinations described in Table 1 to Table 9.

A compound represented by the formula (A-30):

[Chemical Formula 69]

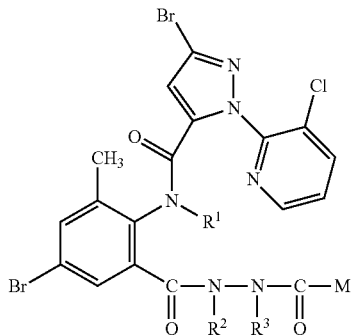
(A-30)

wherein R¹, R², R³ and M represent the combinations described in Table 1 to Table 9.

A compound represented by the formula (A-31):

[Chemical Formula 70]

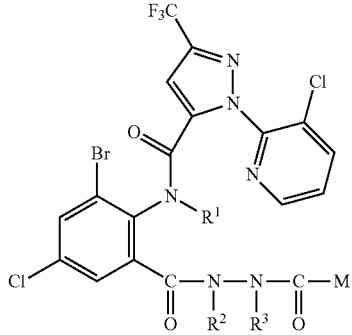
(A-31)

wherein R¹, R², R³ and M represent the combinations described in Table 1 to Table 9.

A compound represented by the formula (A-32):

[Chemical Formula 71]

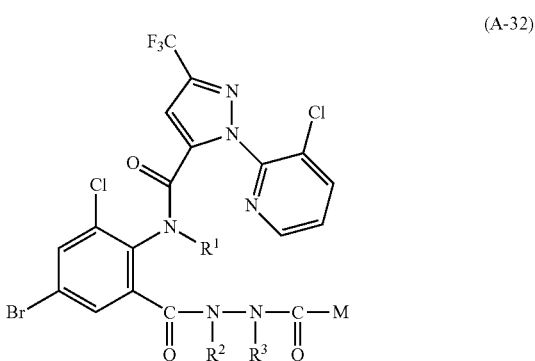
(A-32)

wherein R¹, R², R³ and M represent the combinations described in Table 1 to Table 9.

A compound represented by the formula (A-33):

[Chemical Formula 72]

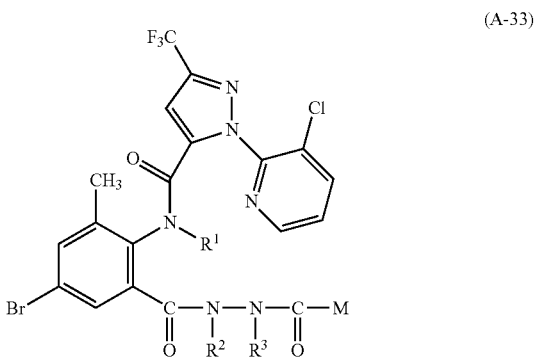
(A-33)

wherein R¹, R², R³ and M represent the combinations described in Table 1 to Table 9.

A compound represented by the formula (A-34):

[Chemical Formula 73]

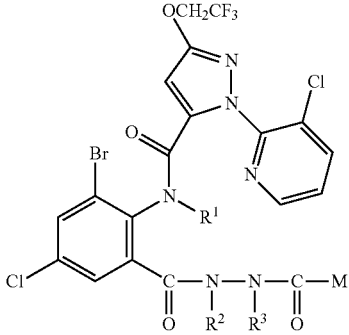
(A-34)

wherein R¹, R², R³ and M represent the combinations described in Table 1 to Table 9.

A compound represented by the formula (A-35):

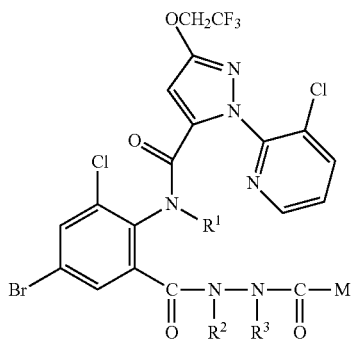

(A-35)

wherein R¹, R², R³ and M represent the combinations described in Table 1 to Table 9.

A compound represented by the formula (A-36):

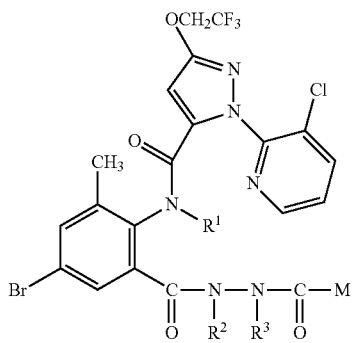

(A-36)

wherein R¹, R², R³ and M represent the combinations described in Table 1 to Table 9.

A compound represented by the formula (B-1):

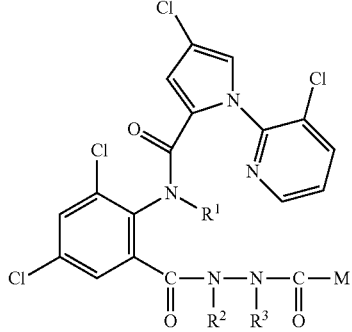

(B-1)

wherein R¹, R², R³ and M represent the combinations described in Table 1 to Table 9.

A compound represented by the formula (B-2):

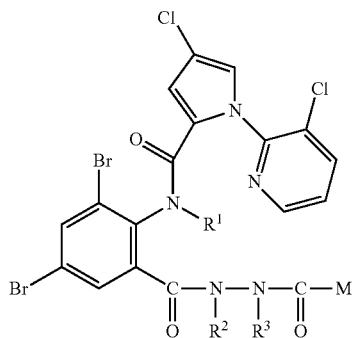

(B-2)

wherein R¹, R², R³ and M represent the combinations described in Table 1 to Table 9.

A compound represented by the formula (B-3):

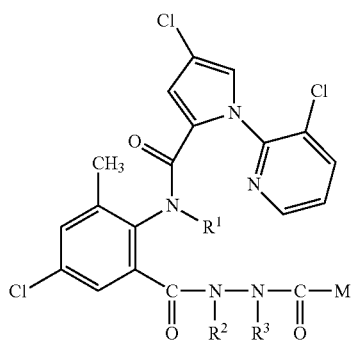

(B-3)

wherein R¹, R², R³ and M represent the combinations described in Table 1 to Table 9.

A compound represented by the formula (B-4):

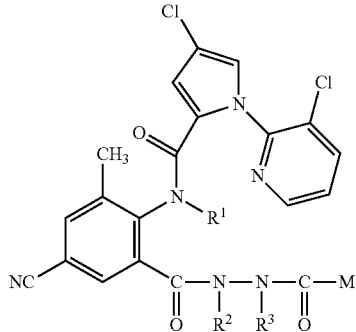

(B-4)

wherein R¹, R², R³ and M represent the combinations described in Table 1 to Table 9.

A compound represented by the formula (B-5):

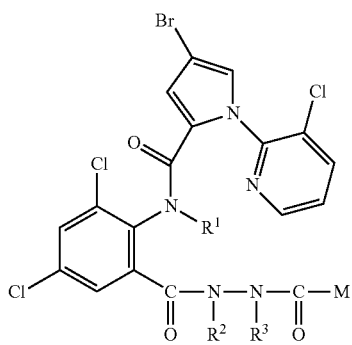

(B-5)

wherein $R^1$, $R^2$, $R^3$ and M represent the combinations described in Table 1 to Table 9.

A compound represented by the formula (B-6):

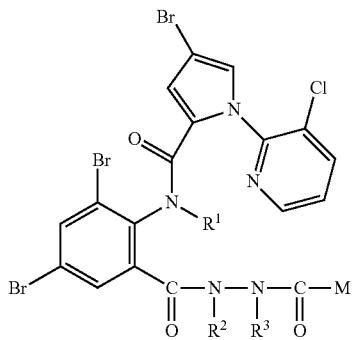

(B-6)

wherein $R^1$, $R^2$, $R^3$ and M represent the combinations described in Table 1 to Table 9.

A compound represented by the formula (B-7):

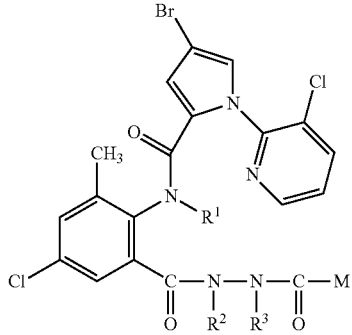

(B-7)

wherein $R^1$, $R^2$, $R^3$ and M represent the combinations described in Table 1 to Table 9.

A compound represented by the formula (B-8):

[Chemical Formula 83]

(B-8)

wherein $R^1$, $R^2$, $R^3$ and M represent the combinations described in Table 1 to Table 9.

A compound represented by the formula (B-9):

[Chemical Formula 84]

(B-9)

wherein $R^1$, $R^2$, $R^3$ and M represent the combinations described in Table 1 to Table 9.

A compound represented by the formula (B-10):

[Chemical Formula 85]

(B-10)

wherein $R^1$, $R^2$, $R^3$ and M represent the combinations described in Table 1 to Table 9.

51

A compound represented by the formula (B-11):

[Chemical Formula 86]

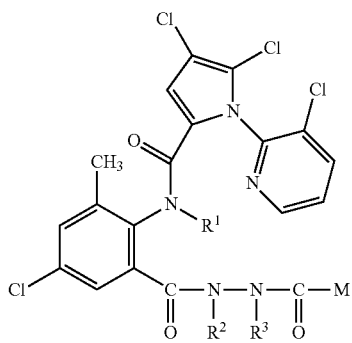

(B-11)

wherein $R^1$, $R^2$, $R^3$ and M the combinations described in Table 1 to Table 9.

A compound represented by the formula (B-12):

[Chemical Formula 87]

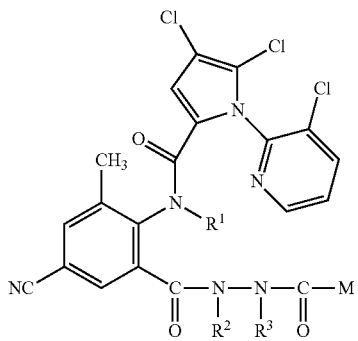

(B-12)

wherein $R^1$, $R^2$, $R^3$ and M represent the combinations described in Table 1 to Table 9.

A compound represented by the formula (B-13):

[Chemical Formula 88]

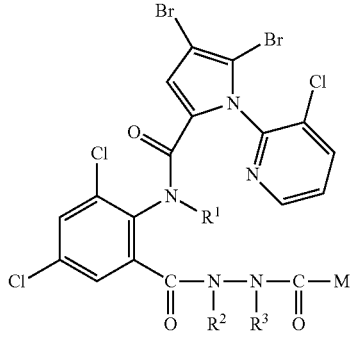

(B-13)

wherein $R^1$, $R^2$, $R^3$ and M represent the combinations described in Table 1 to Table 9.

52

A compound represented by the formula (B-14):

[Chemical Formula 89]

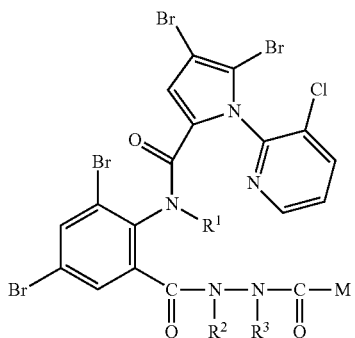

(B-14)

wherein $R^1$, $R^2$, $R^3$ and M represent the combinations described in Table 1 to Table 9.

A compound represented by the formula (B-15):

[Chemical Formula 90]

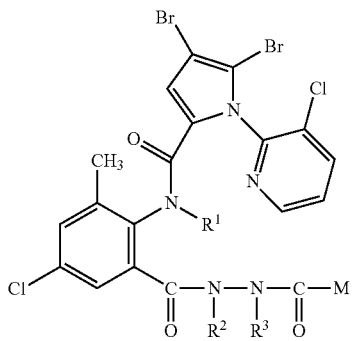

(B-15)

wherein $R^1$, $R^2$, $R^3$ and M represent the combinations described in Table 1 to Table 9.

A compound represented by the formula (B-16):

[Chemical Formula 91]

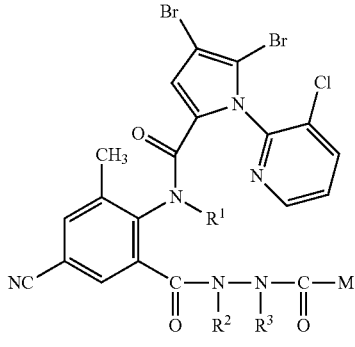

(B-16)

wherein $R^1$, $R^2$, $R^3$ and M represent the combinations described in Table 1 to Table 9.

A compound represented by the formula (C-1):

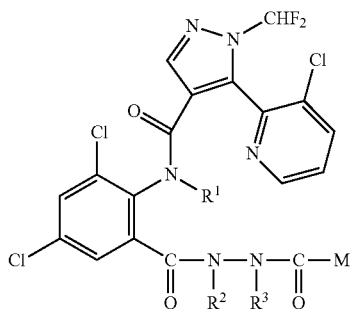

wherein R¹, R², R³ and M represent the combinations described in Table 1 to Table 9.

A compound represented by the formula (C-2):

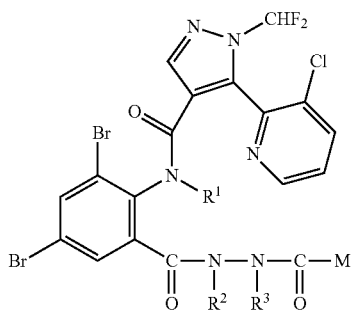

wherein R¹, R², R³ and M represent the combinations described in Table 1 to Table 9.

A compound represented by the formula (C-3):

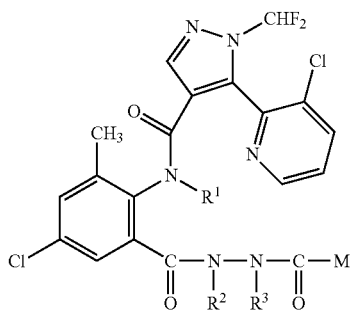

wherein R¹, R², R³ and M represent the combinations described in Table 1 to Table 9.

A compound represented by the formula (C-4):

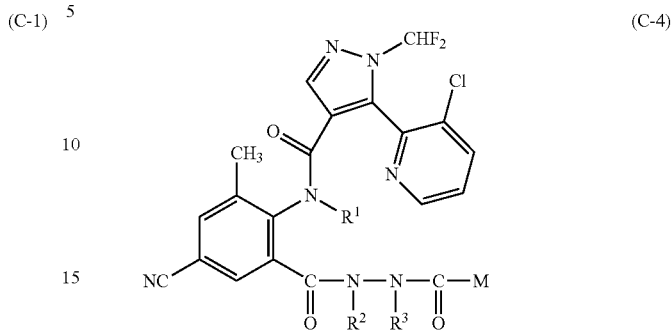

wherein R¹, R², R³ and M represent the combinations described in Table 1 to Table 9.

A compound represented by the formula (C-5):

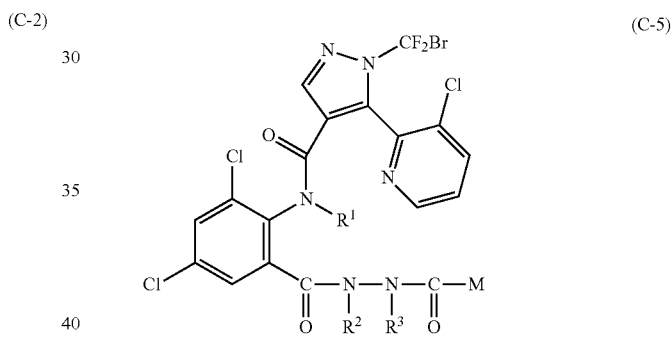

wherein R¹, R², R³ and M represent the combinations described in Table 1 to Table 9.

A compound represented by the formula (C-6):

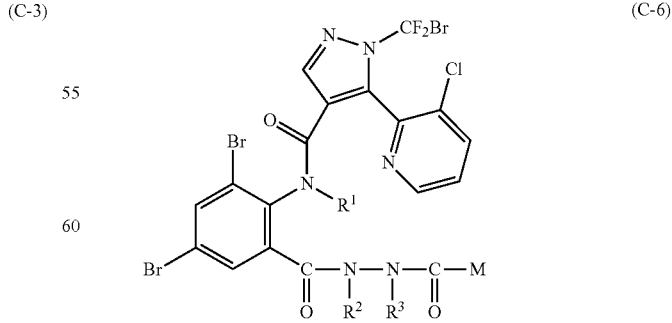

wherein R¹, R², R³ and M represent the combinations described in Table 1 to Table 9.

A compound represented by the formula (C-7):

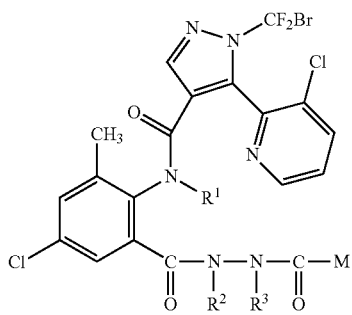

(C-7)

wherein $R^1$, $R^2$, $R^3$ and M represent the combinations described in Table 1 to Table 9.

A compound represented by the formula (C-8):

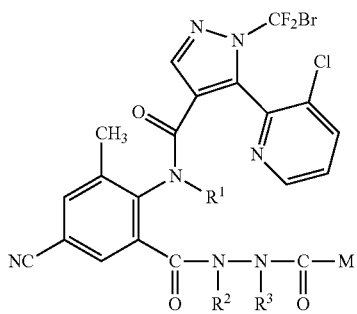

(C-8)

wherein $R^1$, $R^2$, $R^3$ and M represent the combinations described in Table 1 to Table 9.

A compound represented by the formula (C-9):

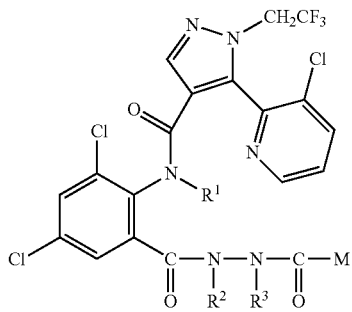

(C-9)

wherein $R^1$, $R^2$, $R^3$ and M represent the combinations described in Table 1 to Table 9.

A compound represented by the formula (C-10):

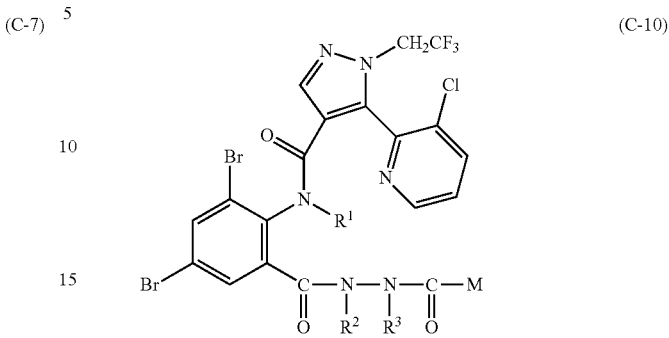

(C-10)

wherein $R^1$, $R^2$, $R^3$ and M represent the combinations described in Table 1 to Table 9.

A compound represented by the formula (C-11):

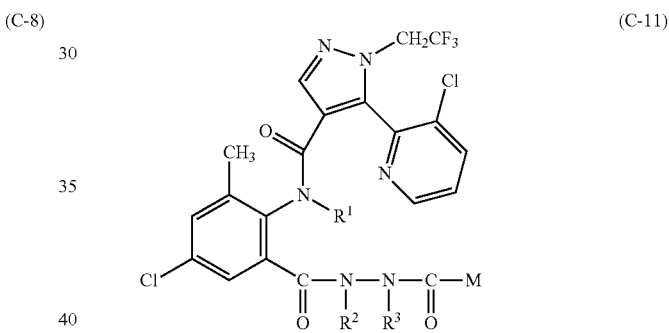

(C-11)

wherein $R^1$, $R^2$, $R^3$ and M represent the combinations described in Table 1 to Table 9.

A compound represented by the formula (C-12):

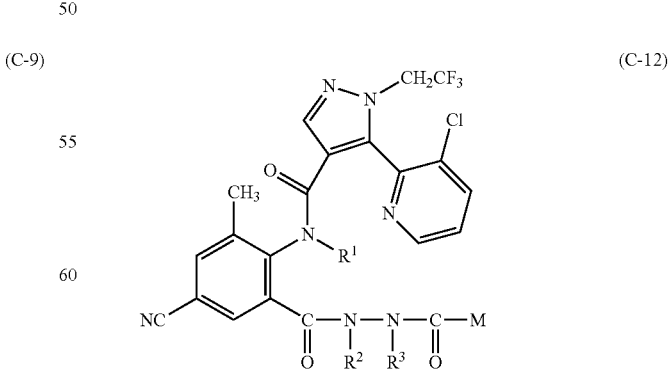

(C-12)

wherein $R^1$, $R^2$, $R^3$ and M represent the combinations described in Table 1 to Table 9.

A compound represented by the formula (D-1):

[Chemical Formula 104]

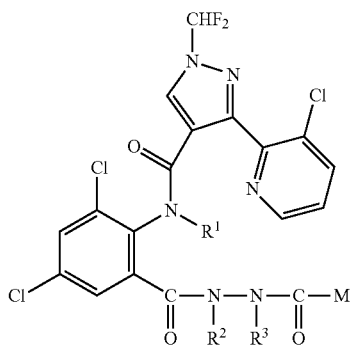
(D-1)

wherein $R^1$, $R^2$, $R^3$ and M represent the combinations described in Table 1 to Table 9.

A compound represented by the formula (D-2):

[Chemical Formula 105]

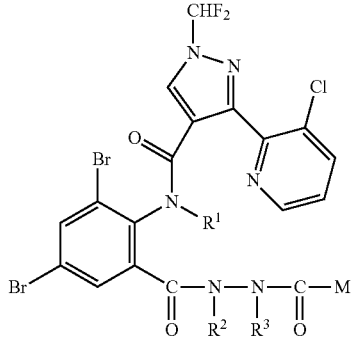
(D-2)

wherein $R^1$, $R^2$, $R^3$ and M represent the combinations described in Table 1 to Table 9.

A compound represented by the formula (D-3):

[Chemical Formula 106]

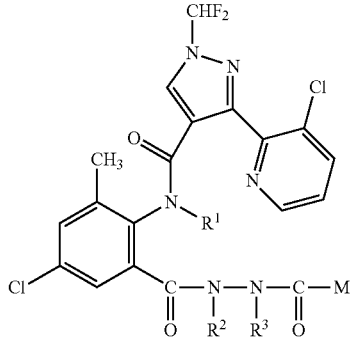
(D-3)

wherein $R^1$, $R^2$, $R^3$ and M represent the combinations described in Table 1 to Table 9.

A compound represented by the formula (D-4):

[Chemical Formula 107]

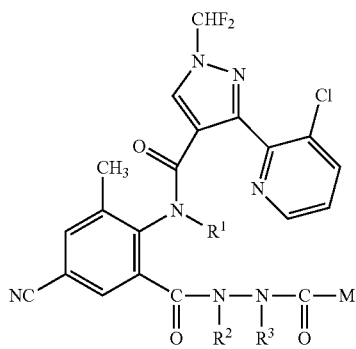
(D-4)

wherein $R^1$, $R^2$, $R^3$ and M represent the combinations described in Table 1 to Table 9.

A compound represented by the formula (D-5):

[Chemical Formula 108]

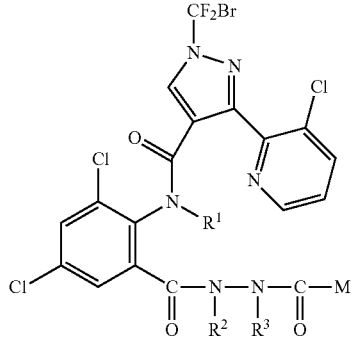
(D-5)

wherein $R^1$, $R^2$, $R^3$ and M represent the combinations described in Table 1 to Table 9.

A compound represented by the formula (D-6):

[Chemical Formula 109]

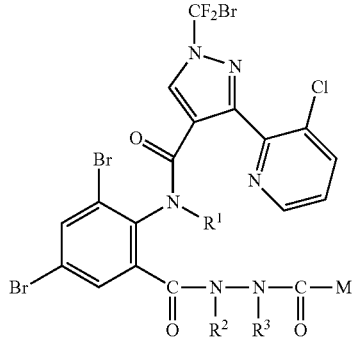
(D-6)

wherein $R^1$, $R^2$, $R^3$ and M represent the combinations described in Table 1 to Table 9.

A compound represented by the formula (D-7):

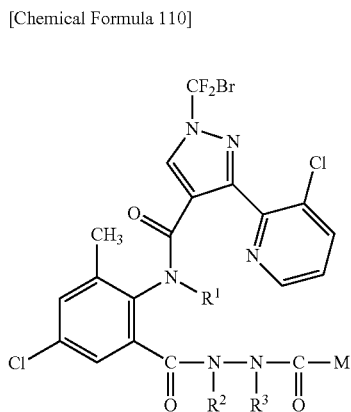

wherein $R^1$, $R^2$, $R^3$ and M represent the combinations described in Table 1 to Table 9.

A compound represented by the formula (D-8):

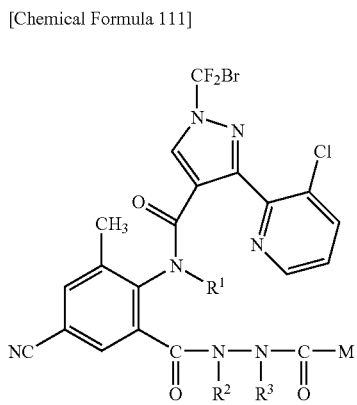

wherein $R^1$, $R^2$, $R^3$ and M represent the combinations described in Table 1 to Table 9.

A compound represented by the formula (D-9):

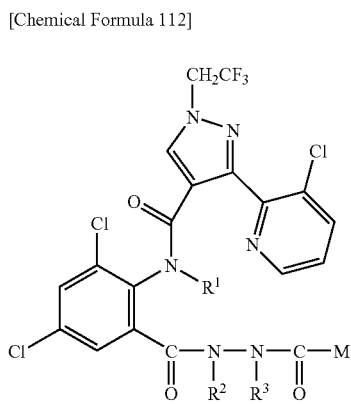

wherein $R^1$, $R^2$, $R^3$ and M represent the combinations described in Table 1 to Table 9.

A compound represented by the formula (D-10):

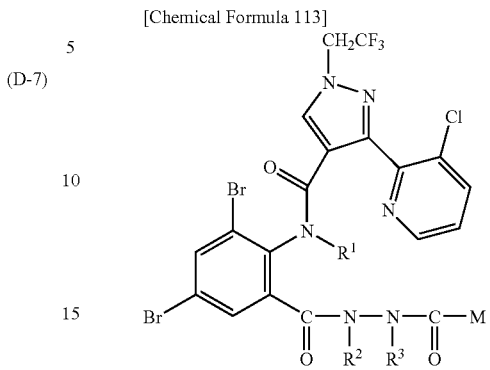

wherein $R^1$, $R^2$, $R^3$ and M represent the combinations described in Table 1 to Table 9.

A compound represented by the formula (D-11):

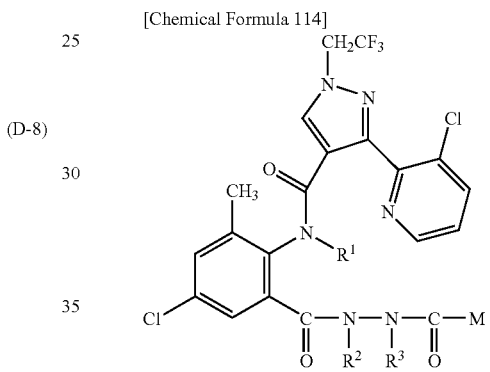

wherein $R^1$, $R^2$, $R^3$ and M represent the combinations described in Table 1 to Table 9.

A compound represented by the formula (D-12):

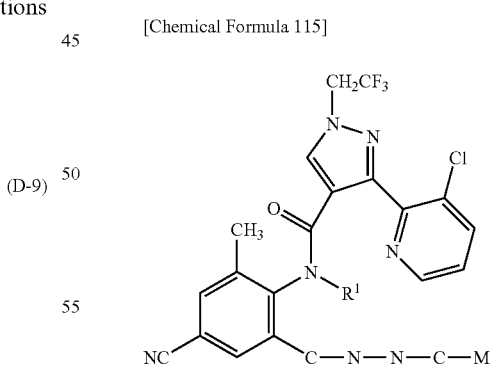

wherein $R^1$, $R^2$, $R^3$ and M represent the combinations described in Table 1 to Table 9.

Harmful arthropods to which the harmful arthropod controlling agent containing the present compound as an active ingredient exhibits a controlling effect include, for example, harmful insects and harmful acarids, and specific examples thereof include the followings.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), spiraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), citrus whitefly (*Dialeurodes citri*), and citrus spiny white fly (*Aleurocanthus spiniferus*); scales (Coccidae) such as Calformia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinis*), and white peach scale (*Pseudaulacaspis pentagona*); lace bugs (Tingidae); cimices such as Cimex lectularius; psyllids (Psyllidae), etc.;

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), *Ostrinia furnacalis*, cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armvworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana* fasciata), smaller tea tortrix (*Adoxophyes* sp.), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); Carposimidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechild moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*), etc.;

Thysanoptera:

Yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), etc.;

Diptera:

Housefly (*Musca domestica*), common mosquito (*Culex pipiens* pallens), horsefly (*Tabanus trigonus*), onion maggot (*Hylemya anitgua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Meditteranean fruit fly (*Ceratitis capitata*), legume leafminer (*Liriomyza trifolii*), tomato leafminer (*Liriomyza sativae*), garden pea leafminer (*Chromatomyia horticola*), etc.;

Coleoptera:

Twenty-eight-spotted ladybird (*Epilachna vigintioctopunctata*), cucurbit leaf beetle (*Aulacophora femoralis*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), pine shoot beetle (*Tomicus piniperda*), etc.;

Orthoptera:

Asiatic locust (*Locusta migratoria*), African mole cricket (*Gryllotalpa africana*), rice grasshopper (*Oxya yezoensis*), rice grasshopper (*Oxya japonica*), etc.;

Hymenoptera:

Cabbage sawfly (*Athalia rosae*), leaf-cutting ant (*Acromyrmex* spp.), fire ant (*Solenopsis* spp.), etc.;

Blattodea:

German cockroach (*Blattella germanica*), smokybrown cockroach (*Periplaneta fuliginosa*), American cockroach (*Periplaneta americana*), *Periplaneta* brunnea, and oriental cockroach (*Blatta orientalis*), etc.;

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta* citri, tomato rust mite (*Aculops lycopersici*), purple tea mite (*Calacarus carinatus*), pink tea rust mite (*Acaphylla theavagran*), and *Eriophyes chibaensis*; tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis, Haemaphysalis flava, Dermacentor taiwanicus, Ixodes ovatus, Ixodes persulcatus, Boophilus microplus*, and *Rhipicephalus sanguineus*; acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides* ptrenyssnus; cheyletide mites (Cheyletidae) such as *Cheyletus eruditus, Cheyletus malaccensis*, and *Cheyletus moorei*; parasitoid mites (Dermanyssidae) such as poultry red mite (*Dermanyssus gallinae*); etc.

The harmful arthropod controlling agent of the present invention can be the present compound as it is. However, it is usually formulated into formulations such as emulsifiable concentrates, oil solutions, dusts, granules, wettable powders, flowable formulations, wettable powders, microcapsule formulations, aerosols, fumigants, poison baits, or resin formulations by mixing the present compound with inert carriers such as solid, liquid or gaseous carriers, and adding surfactants and other auxiliary agents for formulations if necessary. These formulations usually contain 0.1 to 95% by weight of the present compound.

Examples of the solid carrier used for formulation include finely divided powders or granules of clay (e.g., kaolin clay, diatomaceous earth, bentonite, Fubasami clay, and acid clay), synthetic hydrated silicon oxide, talc, ceramics, other inorganic minerals (e.g., sericite, quartz, sulfur, activated carbon, calcium carbonate, and hydrated silica), and chemical fertilizers (e.g., ammonium sulfate, ammonium phosphate, ammonium nitrate, urea, and ammonium chloride).

Examples of the liquid carrier include water, alcohols (e.g., methanol, ethanol, isopropyl alcohol, butanol, hexanol, benzyl alcohol, ethylene glycol, propylene glycol, and phenoxyethanol), ketones (e.g., acetone, methyl ethyl ketone, and cyclohexanone), aromatic hydrocarbons (e.g., toluene, xylene, ethylbenzene, dodecylbenzene, phenylxylylethane, and methylnaphthalene), aliphatic hydrocarbons (e.g., hexane, cyclohexane, kerosene, and gas oil), esters (e.g., ethyl acetate, butyl acetate, isopropyl myristate, ethyl oleate, diisopropyl adipate, diisobutyl adipate, and propylene glycol monomethyl ether acetate), nitriles (e.g., acetonitrile, and isobutyronitrile), ethers (e.g., diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, and 3-methoxy-3-methyl-1-butanol), acid amides (e.g., N,N-dimethylformamide, and N,N-dimethylacetamide), halogenated hydrocarbons (e.g., dichloromethane, trichloroethane, and carbon tetrachloride), sulfoxides (e.g., dimethyl sulfoxide), propylene carbonate and vegetable oils (e.g., soybean oil, and cottonseed oil).

Examples of the gaseous carrier include fluorocarbon, butane gas, LPG (liquefied petroleum gas), dimethyl ether and carbon dioxide gas.

Examples of the surfactant include nonionic surfactants such as polyoxyethylene alkyl ether, polyoxyethylene alkyl aryl ether, and polyethylene glycol fatty acid ester; and anionic surfactants such as alkyl sulfonate, alkylbenzene sulfonate, and alkyl sulfate.

Examples of the other additives for formulations include binders, dispersants, coloring agents and stabilizers, and specific examples thereof include casein, gelatin, saccharides (e.g., starch, gum arabic, cellulose derivatives, and alginic acid), lignin derivatives, bentonite, synthetic water-soluble polymers (e.g., polyvinyl alcohol, polyvinyl pyrrolidone, and polyacrylic acid), PAP (e.g., isopropyl acid phosphate), BHT (2,6-di-tert-butyl-4-methylphenol), and BHA (a mixture of 2-tert-butyl-4-methoxyphenol and 3-tert-butyl-4-methoxyphenol).

The method for controlling harmful arthropods of the present invention is usually carried out by applying the harmful arthropod controlling agent of the present invention directly to harmful arthropods, or applying to habitats (e.g., plants, soils, houses, and animals) of harmful arthropods.

For the method for controlling harmful arthropods of the present invention, the present compound can be used as it is. Usually, the method includes a method comprising formulating the present compound into the harmful arthropod controlling agent of the present invention as described above and applying the harmful arthropod controlling agent to harmful arthropods or a place where harmful arthropods inhabit, for example, by the same method as that of applying a conventional harmful arthropod controlling agent, thereby bringing the harmful arthropod controlling agent to contact with the above harmful arthropods or allowing the harmful arthropods to ingest the harmful arthropod controlling agent.

Examples of the place where harmful arthropods inhabit in the present invention include paddy fields, cultivated lands, orchards, non-crop lands, and houses.

Examples of the application method include spraying treatment, soil treatment, seed treatment, and water culture medium treatment.

The spraying treatment in the present invention is a treatment method which comprises treating plant surfaces or harmful arthropods themselves with the active ingredient (the present compound) to produce a controlling effect on harmful arthropods. Specific examples of the spraying treatment include spraying treatment to foliage, and spraying treatment to tree trunks.

The soil treatment is a treatment method which comprises treating soil or an irrigation liquid with the active ingredient for the purpose of allowing the active ingredient to permeate and transfer into the interior of the plant body of a crop to be protected from damage such as ingestion by harmful arthropods, for example, through the root part of the plant, thereby protecting the crop from damage by harmful arthropods. Specific examples of the soil treatment include planting hole treatment (spraying into planting holes, soil mixing after planting hole treatment), plant foot treatment (plant foot spraying, soil mixing after plant foot treatment, irrigation at plant foot, plant foot treatment at a later seeding raising stage), planting furrow treatment (planting furrow spraying, soil mixing after planting furrow treatment), planting row treatment (planting row spraying, soil mixing after planting row treatment, planting row spraying at a growing stage), planting row treatment at the time of sowing (planting row spraying at the time of sowing, soil mixing after planting row treatment at the time of sowing), broadcast treatment (overall soil surface spraying, soil mixing after broadcast treatment), other soil spraying treatment (spraying of a granular formulation on leaves at a growing stage, spraying under a canopy or around a tree stem, spraying on the soil surface, mixing with surface soil, spraying into seed holes, spraying on the ground surfaces of furrows, spraying between plants), other irrigation treatment (soil irrigation, irrigation at a seedling raising stage, drug solution injection treatment, irrigation of a plant part just above the ground, drug solution drip irrigation, chemigation), seedling raising box treatment (spraying into a seedling raising box, irrigation of a seedling raising box), seedling raising tray treatment (spraying on a seedling raising tray, irrigation of a seedling raising tray), seedbed treatment (spraying on a seedbed, irrigation of a seedbed, spraying on a lowland rice nursery, immersion of seedlings), seedbed soil incorporation treatment (mixing with seedbed soil, mixing with seedbed soil before sowing), and other treatment (mixing with culture soil, plowing under, mixing with surface soil, mixing with soil at the place where raindrops fall from a canopy, treatment at a planting position, spraying of a granule formulation on flower clusters, mixing with a paste fertilizer).

The seed treatment is a treating method which comprises applying the active ingredient directly to or around a seed, a seed tuber or a bulb of a crop to be protected from damage such as ingestion by harmful arthropods to produce a controlling effect on harmful arthropods. Specific examples of the seed treatment include spraying treatment, spray coating treatment, immersion treatment, impregnation treatment, coating treatment, film coating treatment, and pellet coating treatment.

The water culture medium treatment is a treating method which comprises treating a water culture medium or the like with an active ingredient for the purpose of allowing the active ingredient to permeate and transfer into the interior of the plant body of a crop to be protected from damage such as ingestion by harmful arthropods, for example, through the root part of the plant, thereby protecting the crop from damage by harmful arthropods. Specific examples of the water culture medium treatment include mixing with a water culture medium, and incorporation into a water culture medium.

When the harmful arthropod controlling agent of the present invention is used for controlling harmful arthropods in the field of agriculture, the application amount thereof is usually from 1 to 10,000 g of the present compound per 10,000 m$^2$ in terms of the amount of the present compound. When a harmful arthropod controlling agent of the present invention is in the form of a formulation such as an emulsifiable concentrate, a wettable powder or a flowable formulation, the harmful arthropod controlling agent is usually applied after it is diluted with water so that the active ingredient concentration becomes 0.01 to 10,000 ppm. When a harmful arthropod controlling agent is in the form of a formulation such as granules or a powder, the harmful arthropod controlling agent is usually applied as it is.

These harmful arthropod controlling agent and water-dilution thereof can be directly sprayed to harmful arthropods or plants such as crops to be protected from harmful arthropods. Alternatively, soil of a cultivated land can be treated with the harmful arthropod controlling agent or water-dilution thereof in order to control harmful arthropods which inhabit the soil.

The harmful arthropod controlling agent can be in the form of a resin preparation which is processed into a sheet or a string. Such a resin preparation can be applied by winding a crop with a sheet or a string of the resin preparation, putting a string of the resin preparation around a crop so that the crop is surrounded by the string, or laying a sheet of the resin preparation on the soil surface near the root of a crop.

When the harmful arthropod controlling agent of the present invention is used for controlling harmful arthropods living in a house (e.g. fly, mosquito, and cockroach), the application amount thereof is usually from 0.01 to 1,000 mg per 1 m$^2$ in terms of the amount of the present compound in the case of plain surface treatment, and is usually from 0.01 to 500 mg per 1 m$^2$ in terms of the amount of the present compound per in the case of space treatment. When the harmful arthropod controlling agent of the present invention is in the form of a formulation such as an emulsifiable concentrate, a wettable powder or a flowable formulation, the harmful arthropod controlling agent is usually applied after it is diluted with water so that the active ingredient concentration becomes 0.1 to 1,000 ppm. When the harmful arthropod controlling agent of the present invention is in the form of a formulation such as an oil solution, an aerosol formulation, a fumigant or poison bait, the harmful arthropod controlling agent is usually applied as it is.

The present compound can be used a harmful arthropod controlling agent for crop lands such as cultivated lands, paddy fields, lawns and orchards, or non-crop lands.

The harmful arthropod controlling agent of the present invention may further contain, for example, other harmful arthropod controlling agents, acaricides, nematocides, fungicides, herbicides, plant growth regulators, synergists, fertilizers, soil conditioners, and animal feeds.

It is also possible to use the present compound for spraying treatment, soil treatment, seed treatment, and water culture medium treatment as a mixed formulation appropriately prepared by mixing the present compound with harmful organism controlling agents such as insecticides, acaricides, nematocides, fungicides, plant hormone agents, plant growth regulators and herbicides (including isomers and salts thereof), or, for example, synergists, phytotoxicity reducing agents, colorants, and fertilizers.

Examples of the active ingredient of the above other harmful arthropod controlling agents, acaricides and/or nematocides include the followings:

(1) Organophosphorus Compounds
acephate, Aluminium phosphide, butathiofos, cadusafos, chlorethoxyfos, chlorfenvinphos, chlorpyrifos, chlorpyrifos-methyl, cyanophos:CYAP, diazinon, DCIP (dichlorodiisopropyl ether), dichlofenthion:ECP, dichlorvos:DDVP, dimethoate, dimethylvinphos, disulfoton, EPN, ethion, ethoprophos, etrimfos, fenthion:MPP, fenitrothion:MEP, fosthiazate, formothion, Hydrogen phosphide, isofenphos, isoxathion, malathion, mesulfenfos, methidathion:DMTP, monocrotophos, naled BRP, oxydeprofos:ESP, parathion, phosalone, phosmet:PMP, pirimiphos-methyl, pyridafenthion, quinalphos, phenthoate:PAP, profenofos, propaphos, prothiofos, pyraclorfos, salithion, sulprofos, tebupirimfos, temephos, tetrachlorvinphos, terbufos, thiometon, trichlorphon:DEP, and vamidothion;

(2) Carbamate Compounds
alanycarb, bendiocarb, benfuracarb, BPMC carbaryl, carbofuran, carbosulfan, cloethocarb, ethiofencarb, fenobucarb, fenothiocarb, fenoxycarb, furathiocarb, isoprocarb:MIPC, metolcarb, methomyl, methiocarb, NAC, oxamyl, pirimicarb, propoxur:PHC, XMC, thiodicarb, and xylylcarb;

(3) Synthetic Pyrethroid Compounds
acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, 2,3,5,6-tetrafluoro-4-(methoxymethyl)benzyl (EZ)-(1RS,3RS;1RS,3SR)-2,2-dimethyl-3-prop-1-enylcyclopropanecarboxylate, 2,3,5,6-tetrafluoro-4-methylbenzyl (EZ)-(1RS,3RS;1RS,3SR)-2,2-dimethyl-3-prop-1-enylcyclopropanecarboxylate, and 2,3,5,6-tetrafluoro-4-(methoxymethyl)benzyl(1RS,3RS;1RS,3SR)-2,2-dimethyl-3-(2-methyl-1-propenyl) cyclopropanecarboxylate;

(4) Nereistoxin Compounds
cartap, bensultap, thiocyclam, monosultap, and bisultap;

(5) Neonicotinoid Compounds
imidacloprid, nitenpyram, acetamiprid, thiamethoxam, thiacloprid, dinotefuran, and clothianidin;

(6) Benzoylurea Compounds
chlorfluazuron, bistrifluoron, diafenthiuron, diflubenzuron, fluazuron, flucycloxuron, flufenoxuron, hexaflumuron, lufenuron, novaluron, noviflumuron, teflubenzuron, and triflumuron;

(7) Phenyl Pyrazole Compounds
acetoprole, ethiprole, fipronil, vaniliprole, pyriprole, and pyrafluprole;

(8) Bt toxin insecticides viable spores of *Bacillus* thuringinesis and crystal toxins produced therefrom, and a mixture thereof;

(9) Hydrazine Compounds
chromafenozide, halofenozide, methoxyfenozide, and tebufenozide;

(10) Organic Chlorine Compounds
aldrin, dieldrin, dienochlor, endosulfan, and methoxychlor;

(11) Natural Insecticides
machine oil, and nicotine-sulfate;

(12) Other Insecticides
avermectin-B, bromopropylate, buprofezin, chlorphenapyr, cyromazine, D-D(1,3-Dichloropropene), emamectin-benzoate, fenazaquin, flupyrazofos, hydroprene, indoxacarb, metoxadiazone, A(milbemycin-A), pymetrozine, pyridalyl, pyriproxyfen, spinosad, sulfluramid, tolfenpyrad, triazamate, flubendiamide, SI-0009, cyflumetofen, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, nidinotefuran, Potassium oleate, protrifenbute, spiromesifen, Sulfur, metaflumizone, and spirotetramat;
Acaricides
acequinocyl, amitraz, benzoximate, bromopropylate, chinomethionat, chlorobenzilate, CPCBS (chlorfenson), clofentezine, dicofol, etoxazole, fenbutatin oxide, fenothiocarb, fenpyroximate, fluacrypyrim, fluproxyfen, hexythiazox, propargite:BPPS, polynactins, pyridaben, Pyrimidifen, tebufenpyrad, tetradifon, spirodiclofen, amidoflumet, Bifenazate, and Cyflumetofen;
Nematocides (Nematocidal Active Ingredients)
DCIP, fosthiazate, levamisol, methylsothiocyanate, and morantel tartarate.

EXAMPLES

Hereinafter, the present invention will be explained in more detail by way of Preparation Examples, Formulation Examples, and Test Examples, but the present invention is not limited to these Examples.

First, Preparation Examples of the present compound will be explained.

Preparation Example 1

A mixture of 0.24 g of the compound (8-1):

[Chemical Formula 116]

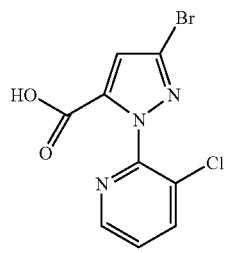

(8-1)

and 0.28 g of thionyl chloride was stirred with heating under reflux for 2 hours. After cooling to room temperature, the reaction mixture was concentrated under reduced pressure to prepare an acid chloride. Then, the acid chloride, 0.19 g of the compound (6-1):

[Chemical Formula 117]

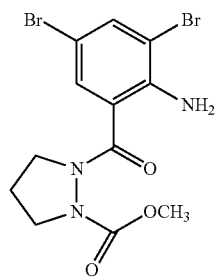

(6-1)

and 2 mL of pyridine were mixed, followed by stirring at room temperature overnight. Into the reaction mixture was poured a mixture of an acid chloride (prepared from 0.12 g of the compound (8-1) in the same manner as described above) and 1 mL of toluene at room temperature, followed by stirring at room temperature overnight. After adding water and toluene, the reaction mixture was concentrated under reduced pressure. After adding water to the residue, the resulting mixture was extracted with ethyl acetate. The organic layer was washed with a saturated sodium chloride solution, dried over anhydrous magnesium sulfate, and concentrated under reduced pressure. The resulting residue was subjected to silica gel column chromatography to obtain 0.19 g of the following present compound (1-1).

The present compound (1-1):

[Chemical Formula 118]

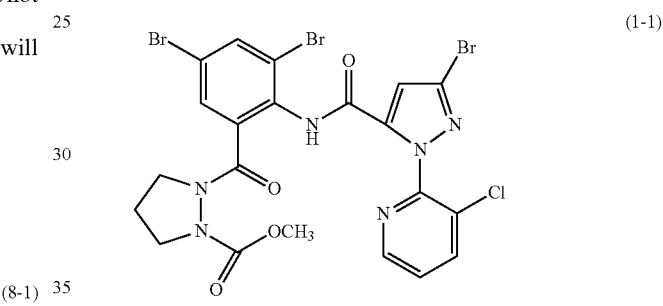

(1-1)

$^1$H-NMR (CDCl$_3$, TMS) δ (ppm): 1.91 (2H, brs), 3.10-3.28 (2H, brm), 3.75-3.85 (5H, brm), 7.20 (1H, brs), 7.38 (1H, dd, J=8 Hz, 5 Hz), 7.60 (1H, brs), 7.69 (1H, d, J=2 Hz), 7.85 (1H, dd, J=8 Hz, 2 Hz), 8.46 (1H, dd, J=5 Hz, 2 Hz), 9.22 (1H, brs)

Preparation Example 2

A mixture of 0.26 g of the compound (6-2):

[Chemical Formula 119]

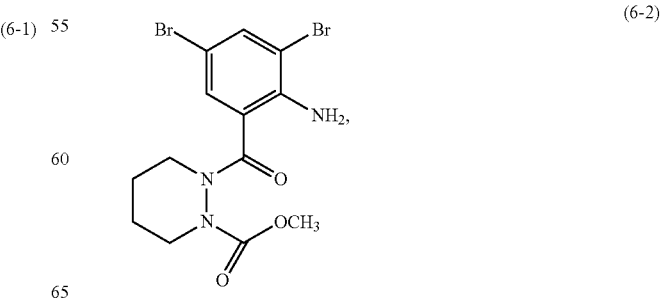

(6-2)

0.18 g of the compound (4-1):

[Chemical Formula 120]

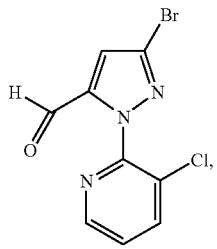
(4-1)

0.18 g of p-chloranil, p-toluenesulfonic acid monohydrate (catalytic amount) and 2 mL of 1,4-dioxane was stirred with heating under reflux in a nitrogen atmosphere for 10 hours. After cooling to room temperature and adding water, the reaction mixture was extracted with ethyl acetate. The organic layer was washed with a saturated sodium chloride solution, dried over anhydrous magnesium sulfate, and concentrated under reduced pressure. The resulting residue was subjected to silica gel column chromatography to obtain 0.26 g of the present compound (1-2).

The present compound (1-2):

[Chemical Formula 121]

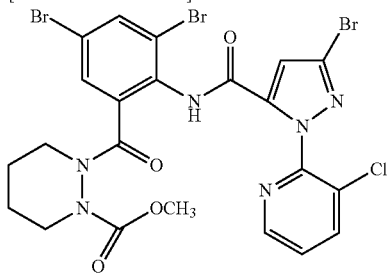
(1-2)

$^1$H-NMR (CDCl$_3$) δ: 1.45-1.80 (4H, m), 2.90-3.00 (2H, m), 3.78 (3H, s), 3.81-3.93 (1H, m), 4.54 (1H, d, J=14 Hz), 7.11 (1H, s), 7.36 (1H, dd, J=8 Hz, 5 Hz), 7.43 (1H, d, J=2 Hz), 7.72 (1H, d, J=2 Hz), 7.85 (1H, d, J=8 Hz), 8.44 (1H, d, J=5 Hz), 9.15 (1H, brs)

Preparation Example 3

A mixture of 0.39 g of the compound (6-3):

[Chemical Formula 122]

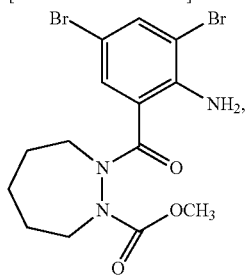
(6-3)

0.26 g of the compound (4-1), 0.26 g of p-chloranil, p-toluenesulfonic acid monohydrate (catalytic amount) and 3 mL of 1,4-dioxane was stirred with heating under reflux in a nitrogen atmosphere for 10 hours. After cooling to room temperature and adding water, the reaction mixture was extracted with ethyl acetate. The organic layer was washed with a saturated sodium chloride solution, dried over anhydrous magnesium sulfate, and concentrated under reduced pressure. The resulting residue was subjected to silica gel column chromatography to obtain 0.43 g of the present compound (1-3).

The present compound (1-3):

[Chemical Formula 123]

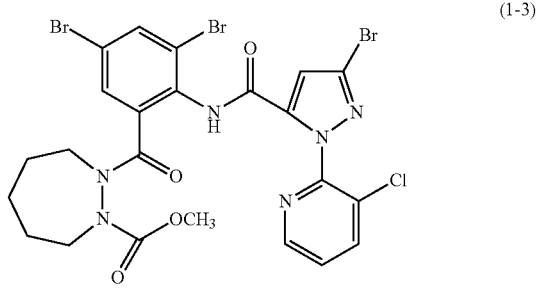
(1-3)

$^1$H-NMR (CDCl$_3$) δ: 1.43-1.98 (6.0H, m), 2.85-2.92 (1.0H, m), 3.40-3.50 (1.0H, m), 3.67-3.83 (4.0H, m), 4.02-4.24 (1.0H, m), 7.10 (0.6H, s), 7.29 (0.4H, s), 7.33-7.39 (2.0H, m), 7.56 (0.2H, s), 7.66 (0.2H, s), 7.73 (0.6H, d, J=2 Hz), 7.82-7.88 (1.0H, m), 8.42-8.47 (1.0H, m), 8.86 (0.2H, s) 9.13 (0.6H, s), 9.43-9.50 (0.2H, m)

Preparation Example 4

To a mixture of 0.30 g of the compound (2-1):

[Chemical Formula 124]

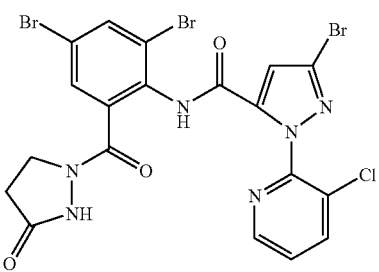
(2-1)

130 μL of triethylamine, 5 mL of acetonitrile and 5 mL of tetrahydrofuran was added 55 μL of methyl chloroformate at room temperature, followed by stirring at room temperature for 3 hours. After adding water, the reaction mixture was extracted with ethyl acetate. The organic layer was washed with a saturated sodium chloride solution, dried over anhydrous magnesium sulfate, and concentrated under reduced pressure. The resulting residue was subjected to silica gel column chromatography to obtain 0.11 g of the present compound (1-4).

[Chemical Formula 125]

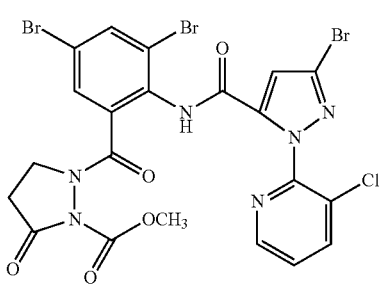
(1-4)

¹H-NMR (CDCl₃) δ: 2.30 (2.0H, t, J=8 Hz), 3.87-3.93 (2.0H, m), 4.04 (3.0H, s), 7.25 (0.6H, s), 7.33-7.34 (0.4H, m), 7.39-7.45 (1.4H, m), 7.56-7.57 (0.6H, m), 7.64-7.69 (1.0H, m), 7.90-7.93 (1.0H, m), 8.44-8.48 (1.0H, m), 8.95-8.99 (0.3H, m), 9.76-9.85 (0.7H, m)

Next, Preparation Examples of the compound (2), the compound (4), the compound (6) and the compound (8) are described as Reference Preparation Examples.

Reference Preparation Example 1

(1) To a mixture of 1.85 g of methyl carbazate and 60 mL of tetrahydrofuran was added 6.0 g of 6,8-dibromo-2H-3,1-benzoxazine-2,4-1H-dion:

[Chemical Formula 126]

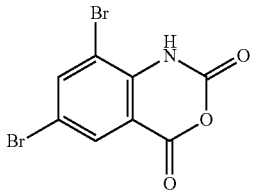

(a compound described in Journal of Organic Chemistry (1947), 12, 743-51) with ice-cooling, followed by stirring with ice-cooling for 3 hours. After warming to room temperature, 0.46 g of methyl carbazate was added to the reaction mixture, followed by stirring at room temperature for 15 hours. The reaction mixture was concentrated under reduced pressure and water was added to the resulting residue, and then the remaining solid was filtered. The solid was washed sequentially with water and ethyl acetate to obtain 4.96 g of N-(2-amino-3,5-dibromobenzoyl)-N'-methoxycarbonylhydrazine.

N-(2-amino-3,5-dibromobenzoyl)-N'-methoxycarbonylhydrazine

¹H-NMR (DMSO-d₆) δ: 3.63 (3H, s), 6.55 (2H, s), 7.71 (1H, s), 7.79 (1H, s), 9.25 (1H, s), 10.32 (1H, s)

(2) To a mixture of 0.50 g of N-(2-amino-3,5-dibromobenzoyl)-N'-methoxycarbonylhydrazine, 0.47 g of potassium carbonate and 5 mL of N,N-dimethylformamide was added 0.36 g of 1,3-dibromopropane was added with ice-cooling, followed by stirring at 50° C. for 10 hours. After adding water, the reaction mixture was extracted with ethyl acetate. The organic layer was washed with water, dried over anhydrous magnesium sulfate, and concentrated under reduced pressure. The resulting residue was subjected to silica gel column chromatography to obtain 0.19 g of the compound (6-1).

Compound (6-1):

[Chemical Formula 127]

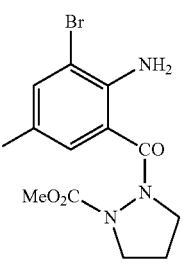

¹H-NMR (CDCl₃, TMS) δ (ppm): 2.14 (2H, quint., J=7 Hz), 3.38-3.57 (2H, brm), 3.76 (3H, s), 3.79-4.13 (2H, brm), 5.33 (2H, brs), 7.43 (1H, d, J=2 Hz), 7.60 (1H, d, J=2 Hz)

Reference Preparation Example 2

A mixture of 1.0 g of N-(2-amino-3,5-dibromobenzoyl)-N'-methoxycarbonylhydrazine (a compound described in Reference Preparation Example 1(1)), 1.13 g of potassium carbonate, 340 µL of 1,4-dibromobutane and 10 mL of N,N-dimethylformamide was stirred at 50° C. for 5 hours. After adding water, the reaction mixture was extracted with ethyl acetate. The organic layer was washed with a saturated sodium chloride solution, dried over anhydrous magnesium sulfate, and concentrated under reduced pressure. The resulting residue was subjected to silica gel column chromatography to obtain 0.26 g of the compound (6-2).

Compound (6-2):

[Chemical Formula 128]

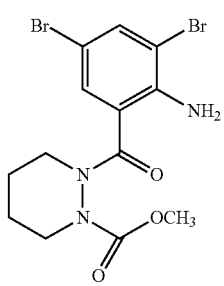
(6-2)

¹H-NMR (CDCl₃) δ: 1.66-1.76 (4H, brm), 3.02-3.05 (2H, brm), 3.75 (3H, s), 4.10-4.45 (2H, m), 4.95 (2H, brs), 7.23 (1H, brs), 7.56 (1H, s)

Reference Preparation Example 3

A mixture of 1.0 g of N-(2-amino-3,5-dibromobenzoyl)-N'-methoxycarbonylhydrazine (a compound described in Reference Preparation Example 1(1)), 1.13 g of potassium carbonate, 410 µL of 1,5-dibromopentane and 10 mL of N,N-dimethylformamide was stirred at 50° C. for 5 hours. After adding water, the reaction mixture was extracted with ethyl acetate. The organic layer was washed with a saturated sodium chloride solution, dried over anhydrous magnesium sulfate, and concentrated under reduced pressure. The resulting residue was subjected to silica gel column chromatography to obtain 0.49 g of the compound (6-3).

Compound (6-3):

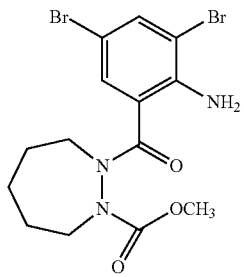

(6-3)

¹H-NMR (CDCl₃) δ: 1.58-1.75 (6.0H, m), 2.93 (0.4H, brs), 3.28-3.42 (1.0H, brm), 3.55-3.84 (4.8H, brm), 3.95 (0.4H, brs), 4.26 (0.4H, brs), 4.78-4.84 (1.4H, m), 5.30 (0.6H, s), 7.07-7.11 (0.3H, m), 7.22-7.25 (0.7H, m), 7.55-7.57 (1.0H, m)

Reference Preparation Example 4

(1) A mixture of 10.7 g of 3-bromo-1H-pyrazole, 11.8 g of 2,3-dichloropyridine, 57.3 g of cesium carbonate and 80 mL of N,N-dimethylformamide was stirred at 100° C. for 8 hours. After cooling to room temperature and adding water, the reaction mixture was extracted twice with methyl tert-butyl ether. The organic layers were combined, washed sequentially with water and a saturated sodium chloride solution, dried over magnesium sulfate, and concentrated under reduced pressure. The resulting residue was subjected to silica gel column chromatography to obtain 12.9 g of 2-(3-bromo-1H-pyrazol-1-yl)-3-chloropyridine. 2-(3-bromo-1H-pyrazol-1-yl)-3-chloropyridine ¹H-NMR (CDCl₃, TMS) δ (ppm): 6.51 (1H, d, J=2 Hz), 7.31 (1H, dd, J=8 Hz, 4 Hz), 7.91 (1H, dd, J=8 Hz, 1Hz), 8.04 (1H, d, J=2 Hz), 8.45 (1H, dd, J=4 Hz, 1Hz)

(2) To a mixture of 9.2 g of 2-(3-bromo-1H-pyrazol-1-yl)-3-chloropyridine and 80 mL of tetrahydrofuran was added dropwise 21.3 mL of a heptane/tetrahydrofuran/ethylbenzene solution of 2.0 M lithium diisopropylamide at −78° C. and then the resulting mixture was stirred at −78° C. for 15 minutes. The mixture was added in a mixture of dry ice and 50 mL of tetrahydrofuran, followed by stirring for 1 hour while warming to about room temperature. After adding water and diethylether to the reaction mixture, an aqueous 2 N sodium hydroxide solution was added to adjust the aqueous layer to pH 10 to 12. The layers were separated and the resulting aqueous layer was washed twice with diethylether and 2 N hydrochloric acid was added so as to adjust the aqueous layer to about pH 3, followed by extraction three times with methyl tert-butyl ether. The organic layers were combined, washed with a saturated sodium chloride solution, dried over magnesium sulfate, and concentrated under reduced pressure to obtain 7.96 g of the compound (8-1).
Compound (8-1)
¹H-NMR (DMSO-d₆) δ (ppm): 7.25 (1H, s), 7.68 (1H, dd, J=8 Hz, 4 Hz), 8.24 (1H, dd, J=8 Hz, J=1 Hz), 8.56 (1H, dd, J=4 Hz, 1Hz)

Reference Preparation Example 5

To a mixture of 5.0 g of 2-(3-bromo-1H-pyrazol-1-yl)-3-chloropyridine (a compound described in Reference Preparation Example 4(1)) and 30 mL of tetrahydrofuran was added dropwise 11.7 mL of a heptane/tetrahydrofuran/ethylbenzene solution of 2.0 M lithium diisopropylamide at −78°

C. To the reaction mixture, a mixture of 3 g of ethyl formate and 10 mL of tetrahydrofuran was added dropwise at −78° C., followed by stirring at room temperature for 2 hours. After adding water, the reaction mixture was extracted with ethyl acetate. The organic layer was washed with water, dried over anhydrous magnesium sulfate, and concentrated under reduced pressure. The resulting residue was subjected to silica gel column chromatography to obtain 3.0 g of the compound (4-1).
Compound (4-1):

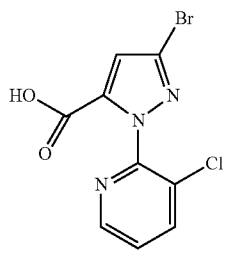

(4-1)

¹H-NMR (CDCl₃, TMS) δ (ppm): 7.11 (1H, s), 7.47 (1H, dd, J=8 Hz, 5 Hz), 7.96 (1H, dd, J=8 Hz, 1Hz), 8.52 (1H, dd, J=5 Hz, 1Hz), 9.79 (1H, s)

Reference Preparation Example 6

(1) A mixture of 1.0 g of the above compound (8-1) and 2 mL of thionyl chloride was heated under reflux for 2 hours. After cooling to room temperature, the reaction mixture was concentrated under reduced pressure and the resulting residue was dissolved in 15 mL of acetonitrile, followed by the addition of 0.88 g of 2-amino-3,5-dibromobenzoic acid and further stirring at room temperature for 30 minutes. To the mixture was added 0.7 mL of triethylamine and the mixture was stirred at room temperature for 30 minutes, followed by the addition of 1.4 mL of triethylamine, stirring at room temperature for 30 minutes, the addition of 0.5 mL of methanesulfonyl chloride and further stirring at room temperature for 5 hours. After adding water, the reaction mixture was concentrated under reduced pressure. The resulting residue was washed with water and methyl tert-butyl ether to obtain 0.80 g of 2-[3-bromo-1-(3-chloro-2-pyridinyl)-1H-pyrazol-5-yl]-6,8-dibromo-4H-3,1-benzoxazin-4-one. 2-[3-bromo-1-(3-chloro-2-pyridinyl)-1H-pyrazol-5-yl]-6,8-dibromo-4H-3,1-benzoxazin-4-one:

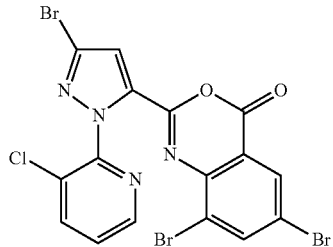

¹H-NMR (DMSO-d₆, TMS) δ (ppm): 7.56 (1H, s), 7.71 (1H, dd, J=8 Hz, 4 Hz), 8.18 (1H, d, J=2 Hz), 8.32 (1H, d, J=8 Hz), 8.35 (1H, d, J=2 Hz), 8.59 (1H, d, J=4 Hz)

(2) A mixture of 2.0 g of 2-[3-bromo-1-(3-chloro-2-pyridinyl)-1H-pyrazol-5-yl]-6,8-dibromo-4H-3,1-benzoxazin-4- one, 0.50 g of 3-pyrazolidinone hydrochloride, 1.18 g of potassium carbonate and 50 mL of tetrahydrofuran was stirred at room temperature for 3 hours. After adding water, the reaction mixture was extracted with ethyl acetate. The organic layer was washed with a saturated sodium chloride solution, dried over anhydrous magnesium sulfate, and concentrated under reduced pressure. The resulting solid was washed with chloroform to obtain 1.56 g of the compound (2-1).
Compound (2-1):

[Chemical Formula 132]

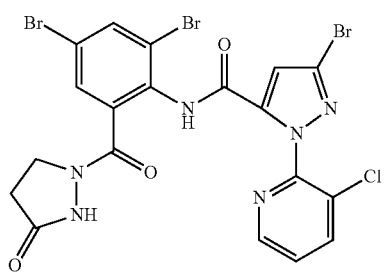

(2-1)

$^1$H-NMR (DMSO-D$_6$) δ 2.18 (1.0H, t, J=8 Hz), 2.39 (1.0H, t, J=8 Hz), 3.68 (1.0H, t, J=8 Hz), 3.81 (1.0H, t, J=8 Hz), 7.14 (0.5H, s), 7.46 (0.5H, s), 7.62 (1.0H, dd, J=8 Hz, 5 Hz), 7.67 (0.5H, d, J=2 Hz), 7.75-7.83 (1.0H, m), 7.95 (0.5H, d, J=2 Hz), 8.10-8.20 (2.0H, m), 8.45-8.52 (1.0H, m), 10.77 (0.5H, s), 11.24-11.50 (0.5H, m)

Next, Formulation Examples are shown. All parts are by weight.

Formulation Example 1

In a mixture of 35 parts of xylene and 35 parts of N,N-dimethylformamide, 10 parts of each of the present compounds (1-1) to (1-4) is dissolved, and then 14 parts of polyoxyethylene styrylphenyl ether and 6 parts of calcium dodecylbenzenesulfonate are added thereto, followed by stirring to obtain a 10% emulsifiable concentrate.

Formulation Example 2

To a mixture of 4 parts of sodium lauryl sulfate, 2 parts of calcium ligninsulfonate, 20 parts of synthetic hydrous silicon oxide fine powder and 54 parts of diatomaceous earth, 20 parts of each of the present compounds (1-1) to (1-4) is added, followed by stirring to obtain a 20% wettable agent.

Formulation Example 3

To 2 parts of each of the present compounds (1-1) to (1-4), 1 part of synthetic hydrous silicon oxide fine powder, 2 parts of calcium ligninsulfonate, 30 parts of bentonite and 65 parts of kaolin clay are added, and then stirred thoroughly. Then, an appropriate amount of water is added to the mixture, followed by stirring, granulation with a granulator and air drying to obtain 2% granules.

Formulation Example 4

In an appropriate amount of acetone, 1 part of each of the present compounds (1-1) to (1-4) is dissolved, and then 5 parts of synthetic hydrous silicon oxide fine powder, 0.3 part of PAP and 93.7 parts of fubasami clay are added, followed by stirring and removal of acetone from the mixture by evaporation to obtain 1% powders.

Formulation Example 5

A mixture of 10 parts of each of the present compounds (1-1) to (1-4), 35 parts of white carbon containing 50 parts of polyoxyethylene alkyl ether sulfate ammonium salt, and 55 parts of water is finely ground by a wet grinding method to obtain a 10% flowable formulation.

Formulation Example 6

In 5 parts of xylene and 5 parts of trichloroethane, 0.1 part of each of the present compounds (1-1) to (1-4) is dissolved, and then solution is mixed with 89.9 parts of deodorized kerosene to obtain a 0.1% oil solution.

Formulation Example 7

In 0.5 mL of acetone, 10 mg of each of the present compounds (1-1) to (1-4) is dissolved and the solution is mixed uniformly with 5 g of a solid feed powder for an animal (solid feed powder for rearing and breeding CE-2, manufactured by CLEA Japan, Inc.), and then dried by evaporation of acetone to obtain poison bait.

Next, harmful arthropod controlling activity of the present compound is shown by Test Examples.

Test Example 1

Each of the flowable formulations of the test compounds (1-1) to (1-4) obtained in Formulation Example 5 was diluted with water so that the active ingredient concentration became 500 ppm to prepare a test spray solution.

On the other hand, cabbage was planted in a polyethylene cup, and grown until the third true leaf or the fourth true leaf was developed. The test spray solution as described above was sprayed in an amount of 20 mL/cup on the cabbage. After the spray solution on the cabbage was dried, 10 third-instar larvae of diamondback moths (*Plutella xylostella*) were put on the cabbage. After 5 days, the number of diamondback moths was counted, and the controlling value was calculated by the following equation.

Controlling value (%)={1−(Cb×Tai)/(Cai×Tb)}×100 wherein Cb represents the number of worms in the non-treated group before treatment, Cai represents the number of worms in the non-treated group on observation, Tb represents the number of worms in the treated group before treatment, and Tai represents the number of worms in the treated group on observation.

As a result, the test spray solution of each of the present compounds (1-1) to (1-4) exhibited a controlling value of 100%.

Test Example 2

Each of the flowable formulations of the test compounds (1-1) to (1-4) obtained in Formulation Example 5 was diluted with water so that the active ingredient concentration became 500 ppm to prepare a test spray solution.

On the other hand, cucumber was planted in a polyethylene cup, and was grown until the first true leaf was developed. About 30 cotton aphids (*Aphis gossypii*) were put on the cucumber. One day after, the test spray solution as described above was sprayed in an amount of 20 mL/cup on the cucumber. Six days after spraying, the number of cotton aphids was counted, and a controlling value was calculated by the following equation.

$$\text{Controlling value (\%)} = \{1-(Cb \times Tai)/(Cai \times Tb)\} \times 100$$

wherein Cb represents the number of worms in the non-treated group before treatment, Cai represents the number of worms in the non-treated group on observation, Tb represents the number of worms in the treated group before treatment, and Tai represents the number of worms in the treated group on observation.

As a result, the test spray solution of each of the present compounds (1-1) to (1-4) exhibited a controlling value of 90% or more.

Test Example 3

Each of the flowable formulations of the test compounds (1-1) to (1-4) obtained in Formulation Example 5 was diluted with water so that the active ingredient concentration became 500 ppm to prepare a test spray solution.

On the other hand, cabbage was planted in a polyethylene cup, and grown until the third true leaf or the fourth true leaf was developed. The test spray solution as described above was sprayed in an amount of 20 mL/cup on the cabbage. After the spray solution sprayed on the cabbage was dried, 10 fourth-instar larvae of common cutworm (*Spodoptera litura*) were put on the cabbage. After 4 days, the number of common cutworm surviving on the cabbage leaves was counted, and a controlling value was calculated by the following equation.

$$\text{Controlling value (\%)} = \{1-(Cb \times Tai)/(Cai \times Tb)\} \times 100$$

wherein Cb represents the number of worms in the non-treated group before treatment, Cai represents the number of worms in the non-treated group on observation, Tb represents the number of worms in the treated group before treatment, and Tai represents the number of worms in the treated group on observation.

As a result, each of the test spray solutions of the present compounds (1-1) to (1-4) exhibited a controlling value of 100%.

Test Example 4

Each of the flowable formulations of the test compounds (1-1) to (1-3) obtained in Formulation Example 5 were diluted with water so that the active ingredient concentration became 500 ppm to prepare a test spray solution.

On the other hand, 20 mL of the test spray solution as described above was sprayed to an apple seedling (28 day-old seeding, tree height: about 15 cm) planted in a plastic cup. The apple seedling was air-dried to such an extent that the spray solution sprayed on the apple seedling was dried, and then about 30 first-instar larvae of summer fruit tortrix (*Adoxophyes orana* fasciata) were released. Seven days after spraying, the number of worms surviving on the apple seedling was counted, and a controlling value was calculated by the following equation.

$$\text{Controlling value (\%)} = \{1-(Cb \times Tai)/(Cai \times Tb)\} \times 100$$

wherein Cb represents the number of worms in the non-treated group before treatment, Cai: the number of worms in the non-treated group on observation, Tb represents the number of worms in the treated group before treatment, and Tai represents the number of worms in the treated group on observation.

As a result, each of the test spray solutions of the present compounds (1-1) to (1-3) exhibited a controlling value of 100%.

Test Example 5

Each of the flowable formulations of the test compounds (1-1) to (1-3) obtained in Formulation Example 5 was diluted with water so that the active ingredient concentration became 500 ppm to prepare a test spray solution.

On the other hand, cucumber was planted in a polyethylene cup, and was grown until the first true leaf was developed. The test spray solution as described above was sprayed in an amount of 20 mL/cup on the cucumber. After the spray solution on the cucumber was dried, the first true leaf was cut and then placed on a filter paper (diameter: 70 mm) containing water in a polyethylene cup (diameter: 110 mm). On the cucumber leaf, 20 larvae of yellow citrus thrips (*Frankliniella occidentalis*) were released, and the polyethylene cup was capped. Seven days after spraying, the number of worms surviving on the cucumber leaf was counted and a controlling value was calculated by the following equation.

$$\text{Controlling value (\%)} = \{1-(Cb \times Tai)/(Cai \times Tb)\} \times 100$$

wherein Cb represents the number of worms in the non-treated group before treatment, Cai represents the number of worms in the non-treated group on observation, Tb represents the number of worms in the treated group before treatment, and Tai represents the number of worms in the treated group on observation.

As a result, the group treated with each of the present compounds (1-1) to (1-3) exhibited a controlling value of 100%.

INDUSTRIAL APPLICABILITY

The present compound has an excellent controlling activity on harmful arthropods and is therefore useful as an active ingredient of a harmful arthropod controlling agent.

The invention claimed is:

1. A hydrazide compound represented by the formula (1):

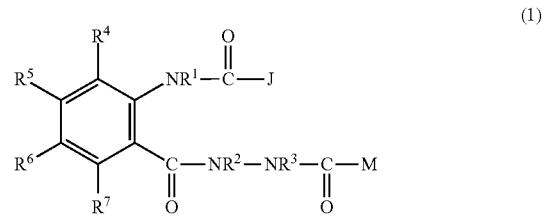

wherein
$R^1$ represents a hydrogen atom, an optionally halogenated C1-C6 alkyl group, a C2-C6 cyanoalkyl group, a C2-C6 alkoxyalkyl group, an optionally halogenated C3-C6 alkenyl group, an optionally halogenated C3-C6 alkynyl group, or a C7-C9 phenylalkyl group whose benzene ring moiety may be substituted with a substituent A shown below;
$R^2$ and $R^3$ are bound at their terminal ends to represent —Z—, and two nitrogen atoms to which $R^2$ and $R^3$ are attached together with Z form a 5- to 8-membered ring, {in which Z is formed by binding a plurality of groups selected from the group consisting of (a) —CH$_2$—, (b) —CH=CH—, (c) —CO—, (d) an oxygen atom, (e) —S(O)$_n$— and (f) —NR$^a$—;

Z may be substituted on its carbon atom(s) with a substituent selected from the group consisting of a halogen atom, an optionally halogenated C1-C6 alkyl group, and an optionally halogenated C2-C6 alkoxycarbonyl group;

n represents an integer of 0 to 2;

$R^a$ represents a hydrogen atom, an optionally halogenated C1-C6 alkyl group, an optionally halogenated C2-C6 alkoxycarbonyl group, or a phenyl group optionally substituted with a substituent A shown below};

$R^4$ represents a halogen atom, or an optionally halogenated C1-C6 alkyl group:

each of $R^5$, $R^6$ and $R^7$ independently represents a hydrogen atom, a halogen atom, a cyano group, or an optionally halogenated C1-C6 alkyl group, or $R^5$ and $R^6$ may be combined to form a 1,3-butadiene-1,4-diyl group optionally substituted with a substituent C shown below;

M represents —$R^8$, —$OR^9$, —$SR^{10}$ or —$NR^{11}R^{12}$,

{in which $R^8$ represents a hydrogen atom, an optionally halogenated C1-C6 alkyl group, a C2-C6 alkoxyalkyl group, an optionally halogenated C2-C6 alkenyl group, or an optionally halogenated C2-C6 alkynyl group;

each of $R^9$, $R^{10}$, $R^{11}$ and $R^{12}$ independently represents an optionally halogenated C1-C6 alkyl group, a C3-C6 alkoxyalkyl group, an optionally halogenated C3-C6 alkenyl group, or an optionally halogenated C3-C6 alkynyl group};

J represents any one of J1 to J3 shown below,

J1:

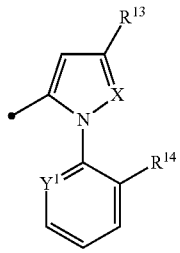

J2:

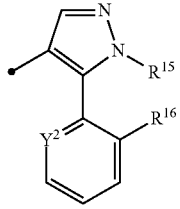

J3:

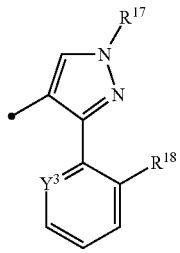

wherein X represents a nitrogen atom or $CR^{19}$;
$Y^1$ represents a nitrogen atom or $CR^{20}$;
$Y^2$ represents a nitrogen atom or $CR^{21}$;
$Y^3$ represents a nitrogen atom or $CR^{22}$;

$R^{13}$ and $R^{19}$ each independently represents a hydrogen atom, a halogen atom, a cyano group, an optionally halogenated C1-C6 alkyl group, an optionally halogenated C1-C6 alkoxy group, an optionally halogenated C1-C6 alkylthio group, an optionally halogenated C1-C6 alkylsulfinyl group, or an optionally halogenated C1-C6 alkylsulfonyl group;

$R^{15}$ and $R^{17}$ each independently represents an optionally halogenated C1-C6 alkyl group;

$R^{14}$, $R^{16}$, $R^{18}$, $R^{20}$, $R^{21}$ and $R^{22}$ each independently represents a hydrogen atom, a halogen atom, or an optionally halogenated C1-C6 alkyl group};

substituent A: a substituent selected from the group consisting of a halogen atom, a cyano group, a nitro group, an optionally halogenated C1-C6 alkyl group, and an optionally halogenated C1-C6 alkoxy group; and substituent C: a substituent selected from the group consisting of a halogen atom, a cyano group, and an optionally halogenated C1-C6 alkyl group.

2. The hydrazide compound according to claim 1, wherein, in the formula (1), Z is any one of Z1 to Z4 shown below:

Z1: —$(CR^{31}R^{32})_m$—
Z2: —$CR^{33}R^{34}$—$CR^{35}$=$CR^{36}$—$CR^{37}R^{38}$—
Z3: —$(CR^{39}R^{40})_2$-Q-$(CR^{41}R^{42})_2$—
Z4: —$(CR^{44}R^{45})_p$—C(=O)—$(CR^{46}R^{47})_q$— in which each of $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{44}$, $R^{45}$, $R^{46}$ and $R^{47}$ independently represents a hydrogen atom or a C1-C4 alkyl group, m represents an integer of 3 to 5, Q represents an oxygen atom, —$S(O)_n$— or —$NR^{43}$—{n represents an integer of 0 to 2, and $R^{43}$ represents a C1-C4 alkyl group}, and p and q each independently represents an integer of 0 to 4, provided that the sum of p and q is 2 to 4.

3. The hydrazide compound according to claim 2, wherein, in the formula (1), Z is any one of Z1 to Z3.

4. The hydrazide compound according to claim 2, wherein, in the formula (1), Z is Z1 or Z4.

5. The hydrazide compound according to claim 2, wherein, in the formula (1), Z is Z1.

6. The hydrazide compound according to claim 1, wherein, in the formula (1), the ring formed by two nitrogen atoms to which $R^2$ and $R^3$ are attached, together with Z is a 5- or 6-membered ring.

7. The hydrazide compound according to claim 1, wherein, in the formula (1), Z is a group formed by binding a plurality of groups selected from the group consisting of (a) —$CH_2$— and (c) —CO— (in which Z may be substituted on its carbon atom(s) with a substituent selected from the group consisting of a halogen atom, an optionally halogenated C1-C6 alkyl group, and an optionally halogenated C2-C6 alkoxycarbonyl group.

8. The hydrazide compound according to claim 1, wherein, in the formula (1), Z is a C3-C6 polymethylene group.

9. A harmful arthropod controlling agent comprising the hydrazide compound according to any one of claims 1 to 8 as an active ingredient.

10. A method for controlling harmful arthropods, which comprises applying the hydrazide compound according to any one of claims 1 to 8 directly to harmful arthropods, or applying to habitats of harmful arthropods.

* * * * *